United States Patent
Shirakawa et al.

(10) Patent No.: US 10,695,385 B2
(45) Date of Patent: Jun. 30, 2020

(54) ORAL CANCER VACCINE

(71) Applicants: National University Corporation Kobe University, Hyogo (JP); Osaka University, Osaka (JP)

(72) Inventors: Toshiro Shirakawa, Hyogo (JP); Takane Katayama, Kyoto (JP); Yoshiko Hashii, Osaka (JP); Keiichi Ozono, Osaka (JP)

(73) Assignees: NATIONAL UNIVERSITY CORPORATION KOBE UNIVERSITY, Hyogo (JP); OSAKA UNIVERSITY, Osaka (JP)

(*) Notice: Subject to any disclaimer, the term of this patent is extended or adjusted under 35 U.S.C. 154(b) by 85 days.

(21) Appl. No.: 15/737,758

(22) PCT Filed: May 30, 2016

(86) PCT No.: PCT/JP2016/065922
§ 371 (c)(1),
(2) Date: Dec. 19, 2017

(87) PCT Pub. No.: WO2016/208332
PCT Pub. Date: Dec. 29, 2016

(65) Prior Publication Data
US 2018/0169156 A1 Jun. 21, 2018

(30) Foreign Application Priority Data

Jun. 25, 2015 (JP) .................. 2015-128034

(51) Int. Cl.

| | | |
|---|---|---|
| *A61K 35/745* | (2015.01) | |
| *C07K 19/00* | (2006.01) | |
| *C07K 14/195* | (2006.01) | |
| *C12N 15/09* | (2006.01) | |
| *A61K 38/00* | (2006.01) | |
| *A61K 38/17* | (2006.01) | |
| *A61K 39/00* | (2006.01) | |
| *C07K 14/47* | (2006.01) | |
| *C12N 15/74* | (2006.01) | |
| *C07K 14/82* | (2006.01) | |

(52) U.S. Cl.
CPC ............ *A61K 35/745* (2013.01); *A61K 38/00* (2013.01); *A61K 38/1764* (2013.01); *A61K 39/0011* (2013.01); *C07K 14/195* (2013.01); *C07K 14/4748* (2013.01); *C07K 19/00* (2013.01); *C12N 15/09* (2013.01); *C12N 15/746* (2013.01); *A61K 2039/522* (2013.01); *A61K 2039/523* (2013.01); *C07K 14/82* (2013.01)

(58) Field of Classification Search
CPC .................................................. A61K 35/745
USPC ...................................................... 424/93.2
See application file for complete search history.

(56) References Cited

U.S. PATENT DOCUMENTS

| | | |
|---|---|---|
| 7,553,636 B2 | 6/2009 | Sung et al. |
| 8,758,760 B2 | 6/2014 | Shirakawa et al. |
| 2010/0247556 A1 | 9/2010 | Sugiyama |
| 2012/0177687 A1 | 7/2012 | Shirakawa et al. |
| 2016/0008459 A1 | 1/2016 | Shirakawa et al. |

FOREIGN PATENT DOCUMENTS

| | | | |
|---|---|---|---|
| EP | 2873726 A1 | 5/2015 | |
| WO | 2007047764 A2 | 4/2007 | |
| WO | 2008149225 A2 | 12/2008 | |
| WO | 2013106834 A2 | 7/2013 | |
| WO | WO-2014129412 A1 * | 8/2014 | ............ A61K 39/12 |
| WO | 2014173542 A1 | 10/2014 | |

OTHER PUBLICATIONS

Buckler et al. (Molecular and Cellular Biology vol. No. 3 ,pp. 1707-1712, Mar. 1991). (Year: 1991).*
International Preliminary Report on Patentability issued in corresponding International Patent Application No. PCT/JP2016/065922 dated Dec. 28, 2017 (6 pages).
International Search Report issued in corresponding International Patent Application No. PCT/JP2016/065922 dated Aug. 2, 2016 (2 pages).
Kitagawa et al., "Development of the Novel Oral Tumor Vaccine Using Bifidobacterium longum Displaying Wilms' Tumor 1 Protein," Molecular Therapy, vol. 24, Supplement 1, May 2016, p. S157.
Sugiyama, H., "WT1 (Wilms' Tumor Gene 1): Biology and Cancer Immunotherapy," Jpn J Clin Oncol, vol. 40(5), 2010, pp. 377-387.
Extended European Search Report issued in corresponding European Patent Application No. 16814103.4 dated Feb. 4, 2019 (12 pages).
Kitagawa et al., "Development of oral caner vaccine using recombinant Bifidobacterium displaying Wilms' tumor 1 protein," Cancer Immunology Immunotherapy, 2017, vol. 66, No. 6, pp. 787-798.
Lindstedt et al., "The WT1 Gene—Its Role in Tumourigenesis and Prospects for Immunotherapeutic Advances," In Vivio, 2014, vol. 28, pp. 675-682.
Shirakawa et al., "Antitumor effect of oral cancer vaccine with Bifidobacterium delivering WT1 protein to gut immune system is superior to WT1 peptide vaccine," Human Vaccines and Immunotherapeutics, 2018, vol. 14, No. 1, pp. 159-162.

(Continued)

*Primary Examiner* — Gary B Nickol
*Assistant Examiner* — Khatol S Shahnan Shah
(74) *Attorney, Agent, or Firm* — Kilyk & Bowersox, P.L.L.C.

(57) ABSTRACT

A cancer vaccine that can be orally administered can be provided through the use of a transformed *Bifidobacterium* capable of expressing and displaying a WT1 protein. The WT1 protein expressed and displayed by the transformed *Bifidobacterium* is a protein covering most of a WT1 protein unlike a WT1 peptide vaccine restricted to a certain HLA. A cancer vaccine using the transformed *Bifidobacterium* as an active ingredient is applicable to patients of various HLA types.

7 Claims, 18 Drawing Sheets
Specification includes a Sequence Listing.

(56) References Cited

OTHER PUBLICATIONS

Takei et al., "Oral administration of genetically modified Bifidobacterium displaying HCV-NS3 multi-epitope fusion protein could induce an HCV-NS3-specific systemic immune response in mice," Vaccine, 2014, vol. 32, No. 25, pp. 3066-3074.

Yamamoto et al., "Genetically modified Bifidobacterium displaying Salmonella-antigen protects mice from lethal challenge of Salmonella Typhimurium in a murine typhoid fever model," Vaccine, 2010, vol. 28, No. 41, pp. 6684-6691.

* cited by examiner

FIG. 1

GNB/LNB SUBSTRATE-BINDING
MEMBRANE PROTEIN (GL-BP) GENE

WT1 PROTEIN

E. coli-B. longum shuttle vector

SPECTINOMYCIN
RESISTANCE GENE

TRANSFER INTO *BIFIDOBACTERIUM*

B. longum
cytoplasm

CONSTRUCTION OF RECOMBINANT *B. LONGUM* EXPRESSING WT1 ANTIGEN PROTEIN
ON SURFACE THEREOF

FIG. 2

PRIMER FOR 410 (SHORT)    PRIMER FOR 420 (LONG)

[bp]

1000→
                                    ←861
500→               ←592

M  410  420  2012  410  420  2012

B. longum 420          B. longum 2012

B. longum 2012 (EXPRESSING GL-BP)          : 46kDa
B. longum 410 (EXPRESSING SHORT GL-BP-WT1): 72.65kDa
B. longum 420 (EXPRESSING LONG GL-BP-WT1) : 82.97kDa

FIG. 4

ANIMAL EXPERIMENTAL PROTOCOL (ANTI-TUMOR EFFECT)

C57BL/6, FEMALE, 6- TO 8-WEEK-OLD (EXPRESSING GL-BP-WT1; CONTROL)+IL-2

◆ SUBCUTANEOUS TRANSPLANTATION OF MURINE WT1-EXPRESSING C1498 CELLS (MURINE LEUKEMIA CELLS) INTO RIGHT FLANK =Day0
$1 \times 10^6$ cells in 200µl RPMI1640 & MATRIGEL /mouse ◆ ADMINISTERED GROUPS (SIX MICE/GROUP) (EVERY OTHER DAY)
$1 \times 10^{10}$ CFU in 100 µl PBS/mouse

- PBS ( CONTROL )
- *B. longum* 2012 (EXPRESSING GL-BP; CONTROL)
- *B. longum* 2012 (EXPRESSING GL-BP; CONTROL) +IL-2
- *B. longum* 420 (EXPRESSING GL-BP-WT1 )
- *B. longum* 420 (EXPRESSING GL-BP-WT1 ) +IL-2

◆ COMBINED USE WITH SUBCUTANEOUS INJECTION OF IL-2 (INTO VICINITY OF TUMOR) (5 DAYS A WEEK)
2000 units in 100 µl PBS/mouse

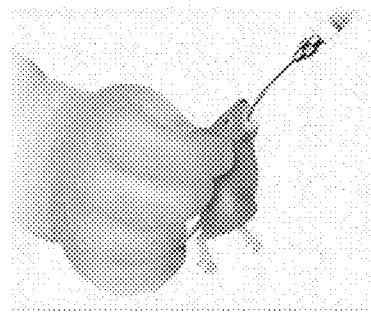

FIG. 5

WT1 ANIMAL EXPERIMENTAL PROTOCOL 

Day 2~Day 30
Oral administration of *BIFIDOBACTERIUM*
($1 \times 10^{10}$ CFU in 100 µl PBS/mouse)
(Every other day, 15 times in total)

4 weeks

Day 0
C1498-WT1
Subcutaneous transplantation into right flank
$1 \times 10^6$ cells in 200µl RPMI1640 & MATRIGEL /mouse Day 2

Day2~31
Subcutaneous injection of IL-2 into vicinity of tumor
(2000IU in 100 µl PBS/mouse)
(5 days a week, 22 times in total)

Day 30

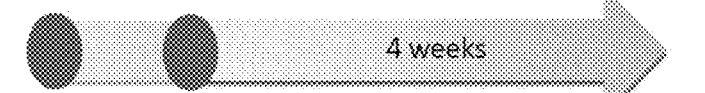

SUBCUTANEOUS TUMOR DIAMETER MEASUREMENT (EVERY 4 DAYS), MEASUREMENT OF MAJOR AXIS AND MINOR AXIS OF TUMOR THROUGH SKIN

PBS

B. longum 420

B. longum 420+IL-2

CHANGE OVER DAYS IN TUMOR VOLUME

PBS: SALINE
420: RECOMBINANT *BIFIDOBACTERIUM* (WITH WT1),
   WT1 ORAL VACCINE
IL-2: INTERLEUKIN-2

FIG. 9

[METHOD]
8-WEEK-OLD C57BL/6N MICE are assigned into the following orally administered groups (N=5), and Vaccine is administered

- B. longum 420 (GLBP-WT1 GENE TRANSFER): 1 × 10$^9$ CFU in 100 μL PBS
- B. longum 2012 (EMPTY VECTOR TRANSFER): 1 × 10$^9$ CFU in 100 μL PBS
- PHOSPHATE-BUFFERED SALINE (PBS): 100 μL

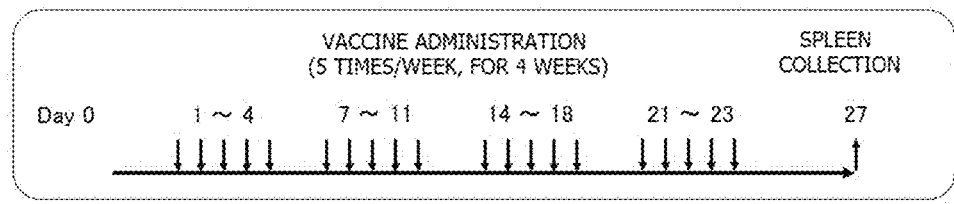

[INVESTIGATION ITEMS]

- MEASUREMENT OF CONCENTRATIONS OF VARIOUS CYTOKINES OF CELLULAR IMMUNE SYSTEM IN SPLENOCYTE CULTURE SUPERNATANT
- DETECTION OF CYTOKINE-PRODUCING T CELLS BY INTRACELLULAR CYTOKINE STAINING OF SPLENOCYTES
- DETECTION OF WT1-SPECIFIC CD8 T CELLS USING WT1 TETRAMER
- MEASUREMENT OF WT1-SPECIFIC CTL ACTIVITY

FIG. 10

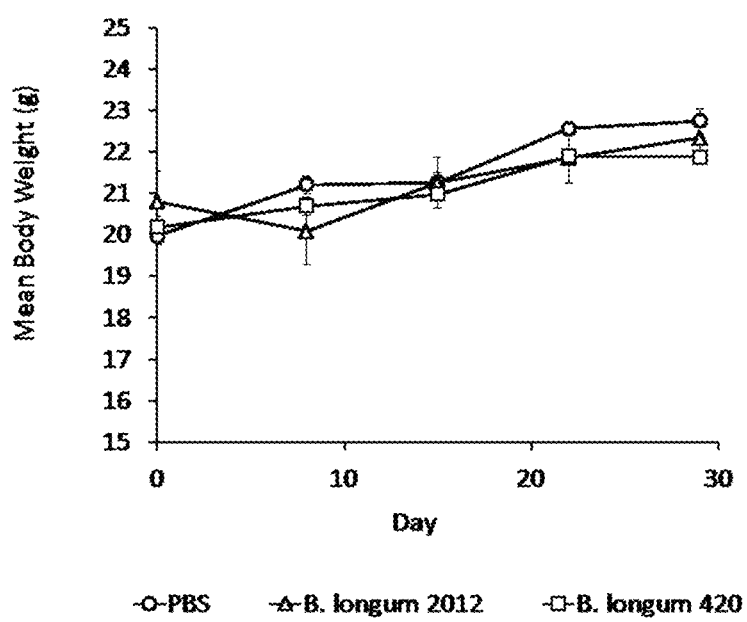

(n=5), *:p<0.01

• Pulse (+) : Stimulated culture with C1498-WT1 cells,   Pulse (-) : Stimulated culture with C1498-MOCK cells

[METHOD]

- $1 \times 10^6$ cells of C1498-WT1 cells or C1498-MOCK cells were subcutaneously inoculated into 6-week-old female C57BL/6N MICE (n=25)

- After 2 days, Mice were assigned into the following orally administered groups (n=5), and Vaccine administration was initiated

- *B. longum* 420 (GLBP-WT1 GENE TRANSFER): $1 \times 10^9$ CFU in 100 μL PBS
  - *B. longum* 2012 (EMPTY VECTOR TRANSFER): $1 \times 10^9$ CFU in 100 μL PBS
  - PBS: 100 μL

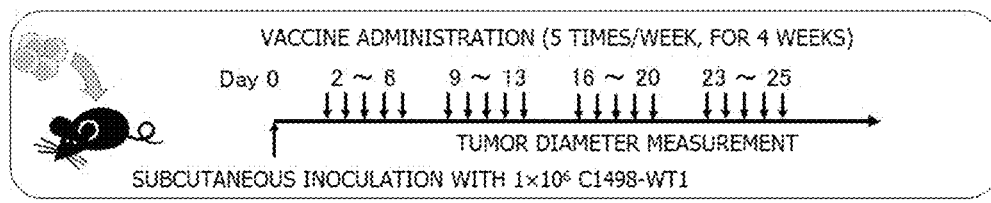

VACCINE ADMINISTRATION (5 TIMES/WEEK, FOR 4 WEEKS)
Day 0   2 ~ 6   9 ~ 13   16 ~ 20   23 ~ 25
TUMOR DIAMETER MEASUREMENT
SUBCUTANEOUS INOCULATION WITH $1 \times 10^6$ C1498-WT1

- Anti-tumor effect was evaluated on the basis of calculated value of the following tumor volume.

[TUMOR VOLUME $mm^3$ = MAJOR AXIS × MINOR AXIS$^2$ × 1/2]

C1498-WT1 inoculation

C1498-Mock inoculation

FIG. 17

[METHOD]
- 1×10⁶ cells of C1498-WT1 cells were subcutaneously inoculated into right dorsal area of 6-week-old female C57BL/6N mice.
- After 7 days, tumor formation was confirmed, mice were assigned into the following orally administered groups (n=3), and Vaccine administration was initiated.

- *B. longum* 420 : 6.4 × 10⁹ CFU in 200 μL PBS
  - *B. longum* 420 : 6.4 × 10⁹ CFU + 10 μg CHOLERA TOXIN (Wako) in 200 μL PBS
  - PBS : 200 μL

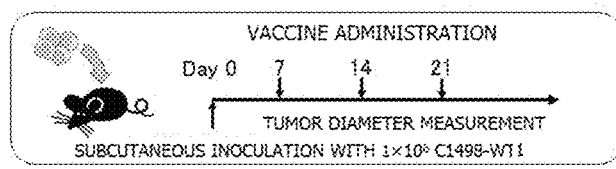

- Vaccine administration was performed three times in total on days 7, 14, and 21 with day of tumor inoculation being defined as day 0. During period from day 0 to day 27, tumor diameter was measured.
  Anti-tumor effect was evaluated on the basis of calculated value of tumor volume.

【TUMOR VOLUME mm³=MAJOR AXIS×MINOR AXIS²×1/2】

FIG. 19

[METHOD]
- 6-week-old female C57BL/6N mice were assigned into the following orally administered groups, and Vaccine administration was performed.

- *B. longum* 420 + 20 µg/dose LTB (Heat-Labile Enterotoxin B subunit ; Sigma) (n=3)
  - *B. longum* 420 + 20 µg/dose MPLA (Monophosphoryl Lipid A ; Sigma) (n=3)
  - *B. longum* 420 + 100 µg/dose Chitosan low molecular weight (Sigma) (n=3)
  - *B. longum* 420 + 10 µg/dose CpG 1585 (Invivogen) (n=2)
  - PBS (n=3)

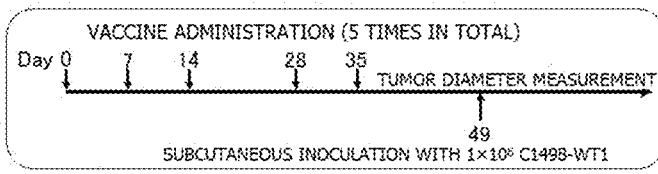

- Each *Bifidobacterium* administration liquid at $6.4 \times 10^9$ CFU/200 µL, or 200 µL of PBS was orally administered to mice using sonde.
- On day 49, C1498-WT1 cells were subcutaneously inoculated into right dorsal area, and during the period until day 76, tumor diameter was measured.
  Anti-tumor effect was evaluated on the basis of calculated value of the following tumor volume.

[ TUMOR VOLUME $mm^3$ = MAJOR AXIS × MINOR $AXIS^2$ × 1/2 ]

GLBP-WT1 : about 82.5 kDa

M: MOLECULAR WEIGHT MARKER

SEQUENCE LISTING

```
<160> NUMBER OF SEQ ID NOS: 26

<210> SEQ ID NO 1
<211> LENGTH: 323
<212> TYPE: PRT
<213> ORGANISM: Mus musculus

<400> SEQUENCE: 1

Pro Ser Gln Ala Ser Ser Gly Gln Ala Arg Met Phe Pro Asn Ala Pro
1               5                   10                  15

Tyr Leu Pro Ser Cys Leu Glu Ser Gln Pro Thr Ile Arg Asn Gln Gly
            20                  25                  30

Tyr Ser Thr Val Thr Phe Asp Gly Ala Pro Ser Tyr Gly His Thr Pro
        35                  40                  45

Ser His His Ala Ala Gln Phe Pro Asn His Ser Phe Lys His Glu Asp
    50                  55                  60

Pro Met Gly Gln Gln Gly Ser Leu Gly Glu Gln Gln Tyr Ser Val Pro
65                  70                  75                  80

Pro Pro Val Tyr Gly Cys His Thr Pro Thr Asp Ser Cys Thr Gly Ser
                85                  90                  95

Gln Ala Leu Leu Leu Arg Thr Pro Tyr Ser Ser Asp Asn Leu Tyr Gln
            100                 105                 110

Met Thr Ser Gln Leu Glu Cys Met Thr Trp Asn Gln Met Asn Leu Gly
        115                 120                 125

Ala Thr Leu Lys Gly Met Ala Ala Gly Ser Ser Ser Val Lys Trp
    130                 135                 140

Thr Glu Gly Gln Ser Asn His Gly Ile Gly Tyr Glu Ser Glu Asn His
145                 150                 155                 160

Thr Ala Pro Ile Leu Cys Gly Ala Gln Tyr Arg Ile His Thr His Gly
                165                 170                 175

Val Phe Arg Gly Ile Gln Asp Val Arg Arg Val Ser Gly Val Ala Pro
            180                 185                 190
```

```
Thr Leu Val Arg Ser Ala Ser Glu Thr Ser Glu Lys Arg Pro Phe Met
        195                 200                 205
Cys Ala Tyr Pro Gly Cys Asn Lys Arg Tyr Phe Lys Leu Ser His Leu
    210                 215                 220
Gln Met His Ser Arg Lys His Thr Gly Glu Lys Pro Tyr Gln Cys Asp
225                 230                 235                 240
Phe Lys Asp Cys Glu Arg Arg Phe Ser Arg Ser Asp Gln Leu Lys Arg
                245                 250                 255
His Gln Arg Arg His Thr Gly Val Lys Pro Phe Gln Cys Lys Thr Cys
                260                 265                 270
Gln Arg Lys Phe Ser Arg Ser Asp His Leu Lys Thr His Thr Arg Thr
            275                 280                 285
His Thr Gly Lys Thr Ser Glu Lys Pro Phe Ser Cys Arg Trp His Ser
        290                 295                 300
Cys Gln Lys Lys Phe Ala Arg Ser Asp Glu Leu Val Arg His His Asn
305                 310                 315                 320
Met His Gln
```

<210> SEQ ID NO 2
<211> LENGTH: 985
<212> TYPE: DNA
<213> ORGANISM: Mus musculus

<400> SEQUENCE: 2

```
ctcgagccgt cccaggcgtc gtcgggccag gcgaggatgt cccgaacgc gccctacctg      60
cccagctgcc tggagtccca gccgacgatc cgcaaccagg gctactccac cgtgacgttc    120
gacggcgccc cgtcctacgg ccacacgccc agccaccacg ccgcccagtt cccgaaccac    180
agcttcaagc acgaagaccc catgggccag cagggcagcc tcggcgaaca gcagtacagc    240
gtgccgccgc cggtctacgg ctgccacacc ccgaccgact cctgcacggg ctcccaggcc    300
ctgctcctgc gtacgccgta ctcctccgac aacctctacc agatgacctc ccagctggag    360
tgcatgacct ggaaccagat gaacctgggc gccacgctga agggaatggc cgcggggtcg    420
tcgagctccg tcaagtggac cgaaggccag tccaaccacg gcatcggcta cgagtccgag    480
aaccacaccg cgccgatcct gtgcggagcc cagtaccgca tccacacgca cggcgtcttc    540
cgcggcatcc aggacgtccg gcgcgtctcc ggcgtcgcgc cgaccctggt gcggtccgcc    600
tccgagacct ccgagaagcg cccgttcatg tgcgcctacc cgggctgcaa caagcgctac    660
ttcaagctct cgcacctgca gatgcactcc cggaagcaca ccggcgagaa gccgtaccag    720
tgcgacttca aggactgcga acgccgcttc tcgcgcagcg accagctgaa gcgccaccag    780
cgtaggcaca ccggcgtgaa gcccttccag tgcaagacct gccagcgcaa gttctcccgc    840
agcgaccacc tcaagacgca cacccgcacc cacaccggca agacgtccga gaagccgttc    900
tcgtgccgct ggcacagctg ccagaagaag ttcgcccgca gcgacgagct cgtgcgccac    960
cacaacatgc accagtgaag catgc                                          985
```

<210> SEQ ID NO 3
<211> LENGTH: 22
<212> TYPE: DNA
<213> ORGANISM: Artificial
<220> FEATURE:
<223> OTHER INFORMATION: Primer for GL-BP (glt-f)

<400> SEQUENCE: 3

```
ggggtgctga tatattggtt tg                                              22
```

<210> SEQ ID NO 4
<211> LENGTH: 31
<212> TYPE: DNA
<213> ORGANISM: Artificial
<220> FEATURE:
<223> OTHER INFORMATION: Primer for GL-BP (glt-r)

<400> SEQUENCE: 4
gctcgagctc ggaaacagac aggccgaagt t                         31

<210> SEQ ID NO 5
<211> LENGTH: 6
<212> TYPE: DNA
<213> ORGANISM: Artificial
<220> FEATURE:
<223> OTHER INFORMATION: Recognition sequence for XhoI

<400> SEQUENCE: 5 ctcgag                                                       6

<210> SEQ ID NO 6
<211> LENGTH: 6
<212> TYPE: DNA
<213> ORGANISM: Artificial
<220> FEATURE:
<223> OTHER INFORMATION: Recognition sequence for SphI

<400> SEQUENCE: 6 gcatgc                                                       6

<210> SEQ ID NO 7
<211> LENGTH: 24
<212> TYPE: DNA
<213> ORGANISM: Artificial
<220> FEATURE:
<223> OTHER INFORMATION: Primer for WT1 (WT1-f)

<400> SEQUENCE: 7
cgctcgagcc gtcccaggcg tcgt                                  24

<210> SEQ ID NO 8
<211> LENGTH: 30
<212> TYPE: DNA
<213> ORGANISM: Artificial
<220> FEATURE:
<223> OTHER INFORMATION: Primer for WT1 (WT1-r2)

<400> SEQUENCE: 8
gcgcatgctc actcgccggt gtgcttccgg                            30

<210> SEQ ID NO 9
<211> LENGTH: 36
<212> TYPE: DNA
<213> ORGANISM: Artificial
<220> FEATURE:
<223> OTHER INFORMATION: Primer (Infusion-F)

<400> SEQUENCE: 9
ggaaaactgt ccatagatgg cgaggcgaac gccacg                     36

<210> SEQ ID NO 10
<211> LENGTH: 36
<212> TYPE: DNA
<213> ORGANISM: Artificial
<220> FEATURE:

<223> OTHER INFORMATION: Primer (Infusion-R)

<400> SEQUENCE: 10
tttcatctgt gcatagtgct gcaaggcgat taagtt                36

<210> SEQ ID NO 11
<211> LENGTH: 23
<212> TYPE: DNA
<213> ORGANISM: Artificial
<220> FEATURE:
<223> OTHER INFORMATION: Primer (410, 420-F)

<400> SEQUENCE: 11
acgatccgca accagggcta ctc                23

<210> SEQ ID NO 12
<211> LENGTH: 23
<212> TYPE: DNA
<213> ORGANISM: Artificial
<220> FEATURE:
<223> OTHER INFORMATION: Primer (410-R)

<400> SEQUENCE: 12
ggtgcgagag cttgaagtag cgc                23

<210> SEQ ID NO 13
<211> LENGTH: 22
<212> TYPE: DNA
<213> ORGANISM: Artificial
<220> FEATURE:
<223> OTHER INFORMATION: Primer (420-R)

<400> SEQUENCE: 13
gtcgctgcgg gcgaacttct tc                22

<210> SEQ ID NO 14
<211> LENGTH: 323
<212> TYPE: PRT
<213> ORGANISM: Homo sapiens

<400> SEQUENCE: 14

```
Pro Ser Gln Ala Ser Ser Gly Gln Ala Arg Met Phe Pro Asn Ala Pro
1               5                   10                  15

Tyr Leu Pro Ser Cys Leu Glu Ser Gln Pro Ala Ile Arg Asn Gln Gly
            20                  25                  30

Tyr Ser Thr Val Thr Phe Asp Gly Thr Pro Ser Tyr Gly His Thr Pro
        35                  40                  45

Ser His His Ala Ala Gln Phe Pro Asn His Ser Phe Lys His Glu Asp
    50                  55                  60

Pro Met Gly Gln Gln Gly Ser Leu Gly Glu Gln Gln Tyr Ser Val Pro
65                  70                  75                  80

Pro Pro Val Tyr Gly Cys His Thr Pro Thr Asp Ser Cys Thr Gly Ser
                85                  90                  95

Gln Ala Leu Leu Leu Arg Thr Pro Tyr Ser Ser Asp Asn Leu Tyr Gln
            100                 105                 110

Met Thr Ser Gln Leu Glu Cys Met Thr Trp Asn Gln Met Asn Leu Gly
        115                 120                 125

Ala Thr Leu Lys Gly Val Ala Ala Gly Ser Ser Ser Ser Val Lys Trp
    130                 135                 140

Thr Glu Gly Gln Ser Asn His Ser Thr Gly Tyr Glu Ser Asp Asn His
145                 150                 155                 160
```

```
Thr Thr Pro Ile Leu Cys Gly Ala Gln Tyr Arg Ile His Thr His Gly
            165                 170                 175

Val Phe Arg Gly Ile Gln Asp Val Arg Arg Val Pro Gly Val Ala Pro
        180                 185                 190

Thr Leu Val Arg Ser Ala Ser Glu Thr Ser Glu Lys Arg Pro Phe Met
            195                 200                 205

Cys Ala Tyr Pro Gly Cys Asn Lys Arg Tyr Phe Lys Leu Ser His Leu
        210                 215                 220

Gln Met His Ser Arg Lys His Thr Gly Glu Lys Pro Tyr Gln Cys Asp
225                 230                 235                 240

Phe Lys Asp Cys Glu Arg Arg Phe Ser Arg Ser Asp Gln Leu Lys Arg
                245                 250                 255

His Gln Arg Arg His Thr Gly Val Lys Pro Phe Gln Cys Lys Thr Cys
            260                 265                 270

Gln Arg Lys Phe Ser Arg Ser Asp His Leu Lys Thr His Thr Arg Thr
        275                 280                 285

His Thr Gly Lys Thr Ser Glu Lys Pro Phe Ser Cys Arg Trp Pro Ser
    290                 295                 300

Cys Gln Lys Lys Phe Ala Arg Ser Asp Glu Leu Val Arg His His Asn
305                 310                 315                 320

Met His Gln

<210> SEQ ID NO 15
<211> LENGTH: 973
<212> TYPE: DNA
<213> ORGANISM: Homo sapiens

<400> SEQUENCE: 15
ccgtcccagg cgtcgtcggg ccaggcgagg atgttcccga acgcgcccta cctgcccagc    60
tgcctggagt cccagccggc gatccgcaac cagggctact ccaccgtgac gttcgacggc   120
accccgtcct acggccacac gcccagccac cacgccgccc agttcccgaa ccacagcttc   180
aagcacgaag accccatggg ccagcagggc agcctcggcg aacagcagta cagcgtgccg   240
ccgccggtct acgctgcca cccccgacc gactcctgca cgggctccca ggccctgctc   300
ctgcgtacgc cgtactcctc cgacaacctc taccagatga cctcccagct ggagtgcatg   360
acctggaacc agatgaacct gggcgccacg ctgaaggag cgccgcggg gtcgtcgagc   420
tccgtcaagt ggaccgaagg ccagtccaac cactccaccg gctacgagtc cgacaaccac   480
accacgccga tcctgtgcgg agcccagtac cgcatccaca cgcacggcgt cttccgcggc   540
atccaggacg tccggcgcgt ccccggcgtc gcgccgaccc tggtgcggtc cgcctccgag   600
acctccgaga agcgcccgtt catgtgcgcc taccggggct gcaacaagcg ctacttcaag   660
ctctcgcacc tgcagatgca ctcccggaag cacaccggcg agaagccgta ccagtgcgac   720
ttcaaggact gcgaacgccg cttctcgcgc agcgaccagc tgaagcgcca ccagcgtagg   780
cacaccggcg tgaagccctt ccagtgcaag acctgccagc gcaagttctc ccgcagcgac   840
cacctcaaga cgcacacccg cacccacacc ggcaagacgt ccgagaagcc gttctcgtgc   900
cgctggccca gctgccagaa gaagttcgcc cgcagcgacg agctcgtgcg ccaccacaac   960
atgcaccagt gaa                                                     973

<210> SEQ ID NO 16
<211> LENGTH: 323
<212> TYPE: PRT
```

<213> ORGANISM: Homo sapiens

<400> SEQUENCE: 16

Pro Ser Gln Ala Ser Ser Gly Gln Ala Arg Met Phe Pro Asn Ala Pro
1               5                   10                  15

Tyr Leu Pro Ser Cys Leu Glu Ser Gln Pro Ala Ile Arg Asn Gln Gly
            20                  25                  30

Tyr Ser Thr Val Thr Phe Asp Gly Thr Pro Ser Tyr Gly His Thr Pro
        35                  40                  45

Ser His His Ala Ala Gln Phe Pro Asn His Ser Phe Lys His Glu Asp
    50                  55                  60

Pro Met Gly Gln Gln Gly Ser Leu Gly Glu Gln Gln Tyr Ser Val Pro
65                  70                  75                  80

Pro Pro Val Tyr Gly Cys His Thr Pro Thr Asp Ser Cys Thr Gly Ser
                85                  90                  95

Gln Ala Leu Leu Leu Arg Thr Pro Tyr Ser Ser Asp Asn Leu Tyr Gln
            100                 105                 110

Met Thr Ser Gln Leu Glu Cys Tyr Thr Trp Asn Gln Met Asn Leu Gly
        115                 120                 125

Ala Thr Leu Lys Gly Val Ala Ala Gly Ser Ser Ser Ser Val Lys Trp
    130                 135                 140

Thr Glu Gly Gln Ser Asn His Ser Thr Gly Tyr Glu Ser Asp Asn His
145                 150                 155                 160

Thr Thr Pro Ile Leu Cys Gly Ala Gln Tyr Arg Ile His Thr His Gly
                165                 170                 175

Val Phe Arg Gly Ile Gln Asp Val Arg Arg Val Pro Gly Val Ala Pro
            180                 185                 190

Thr Leu Val Arg Ser Ala Ser Glu Thr Ser Glu Lys Arg Pro Phe Met
        195                 200                 205

Cys Ala Tyr Pro Gly Cys Asn Lys Arg Tyr Phe Lys Leu Ser His Leu
    210                 215                 220

Gln Met His Ser Arg Lys His Thr Gly Glu Lys Pro Tyr Gln Cys Asp
225                 230                 235                 240

Phe Lys Asp Cys Glu Arg Arg Phe Ser Arg Ser Asp Gln Leu Lys Arg
                245                 250                 255

His Gln Arg Arg His Thr Gly Val Lys Pro Phe Gln Cys Lys Thr Cys
            260                 265                 270

Gln Arg Lys Phe Ser Arg Ser Asp His Leu Lys Thr His Thr Arg Thr
        275                 280                 285

His Thr Gly Lys Thr Ser Glu Lys Pro Phe Ser Cys Arg Trp Pro Ser
    290                 295                 300

Cys Gln Lys Lys Phe Ala Arg Ser Asp Glu Leu Val Arg His His Asn
305                 310                 315                 320

Met His Gln

<210> SEQ ID NO 17
<211> LENGTH: 973
<212> TYPE: DNA
<213> ORGANISM: Homo sapiens

<400> SEQUENCE: 17
ccgtcccagg cgtcgtcggg ccaggcgagg atgttcccga acgcgcccta cctgccagc      60 tgcctggagt cccagccggc gatccgcaac cagggctact ccaccgtgac gttcgacggc    120 acccccgtcct acggccacac gcccagccac acgccgcccc agttcccgaa ccacagcttc    180

```
aagcacgaag accccatggg ccagcagggc agcctcggcg aacagcagta cagcgtgccg    240
ccgccggtct acggctgcca caccccgacc gactcctgca cgggctccca ggccctgctc    300
ctgcgtacgc cgtactcctc cgacaacctc taccagatga cctcccagct ggagtgctac    360
acctggaacc agatgaacct gggcgccacg ctgaagggag tcgccgcggg gtcgtcgagc    420
tccgtcaagt ggaccgaagg ccagtccaac cactccaccg gctacgagtc cgacaaccac    480
accacgccga tcctgtgcgg agcccagtac cgcatccaca cgcacggcgt cttccgcggc    540
atccaggacg tccggcgcgt ccccggcgtc gcgccgaccc tggtgcggtc cgcctccgag    600
acctccgaga agcgcccgtt catgtgcgcc tacccgggct gcaacaagcg ctacttcaag    660
ctctcgcacc tgcagatgca ctcccggaag cacaccggcg agaagccgta ccagtgcgac    720
ttcaaggact gcgaacgccg cttctcgcgc agcgaccagc tgaagcgcca ccagcgtagg    780
cacaccggcg tgaagccctt ccagtgcaag acctgccagc gcaagttctc ccgcagcgac    840
cacctcaaga cgcacacccg cacccacacc ggcaagacgt ccgagaagcc gttctcgtgc    900
cgctggccca gctgccagaa gaagttcgcc cgcagcgacg agctcgtgcg ccaccacaac    960
atgcaccagt gaa                                                      973
```

<210> SEQ ID NO 18
<211> LENGTH: 16
<212> TYPE: PRT
<213> ORGANISM: Artificial Sequence
<220> FEATURE:
<223> OTHER INFORMATION: T cell epitope np332

<400> SEQUENCE: 18

Lys Arg Tyr Phe Lys Leu Ser His Leu Gln Met His Ser Arg Lys His
1               5                   10                  15

<210> SEQ ID NO 19
<211> LENGTH: 9
<212> TYPE: PRT
<213> ORGANISM: Artificial Sequence
<220> FEATURE:
<223> OTHER INFORMATION: T cell epitope np126

<400> SEQUENCE: 19

Arg Met Phe Pro Asn Ala Pro Tyr Leu
1               5

<210> SEQ ID NO 20
<211> LENGTH: 9
<212> TYPE: PRT
<213> ORGANISM: Artificial Sequence
<220> FEATURE:
<223> OTHER INFORMATION: T cell epitope n187

<400> SEQUENCE: 20

Ser Leu Gly Glu Gln Gln Tyr Ser Val
1               5

<210> SEQ ID NO 21
<211> LENGTH: 9
<212> TYPE: PRT
<213> ORGANISM: Artificial Sequence
<220> FEATURE:
<223> OTHER INFORMATION: T cell epitope n235

<400> SEQUENCE: 21

Cys Met Thr Trp Asn Gln Met Asn Leu

<210> SEQ ID NO 22
<211> LENGTH: 449
<212> TYPE: PRT
<213> ORGANISM: Mus musculus

<400> SEQUENCE: 22

Met Gly Ser Asp Val Arg Asp Leu Asn Ala Leu Leu Pro Ala Val
1               5                   10                  15

Ser Leu Gly Gly Gly Gly Gly Cys Gly Leu Pro Val Ser Gly Ala
                20                  25                  30

Arg Gln Trp Ala Pro Val Leu Asp Phe Ala Pro Pro Gly Ala Ser Ala
        35                  40                  45

Tyr Gly Ser Leu Gly Gly Pro Ala Pro Pro Ala Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Leu His Phe
                85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
    115                 120                 125

Pro Asn Ala Pro Tyr Leu Pro Ser Cys Leu Glu Ser Gln Pro Thr Ile
130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
        260                 265                 270

Ser Glu Asn His Thr Ala Pro Ile Leu Cys Gly Ala Gln Tyr Arg Ile
        275                 280                 285

His Thr His Gly Val Phe Arg Gly Ile Gln Asp Val Arg Arg Val Ser
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
        355                 360                 365

```
Gln Leu Lys Arg His Gln Arg Arg His Thr Gly Val Lys Pro Phe Gln
        370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
            435                 440                 445

Leu

<210> SEQ ID NO 23
<211> LENGTH: 449
<212> TYPE: PRT
<213> ORGANISM: Homo sapiens

<400> SEQUENCE: 23

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro Pro Pro
    50                  55                  60

Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285
```

His Thr His Gly Val Phe Arg Gly Ile Gln Asp Val Arg Arg Val Pro
        290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 24
<211> LENGTH: 30
<212> TYPE: DNA
<213> ORGANISM: Artificial Sequence
<220> FEATURE:
<223> OTHER INFORMATION: Primer F:430

<400> SEQUENCE: 24
atgacctccc agctggagtg catgacctgg                                    30

<210> SEQ ID NO 25
<211> LENGTH: 30
<212> TYPE: DNA
<213> ORGANISM: Artificial Sequence
<220> FEATURE:
<223> OTHER INFORMATION: Primer F:440

<400> SEQUENCE: 25
atgacctccc agctggagtg ctacacctgg                                    30

<210> SEQ ID NO 26
<211> LENGTH: 32
<212> TYPE: DNA
<213> ORGANISM: Artificial Sequence
<220> FEATURE:
<223> OTHER INFORMATION: Primer R: 430, 440

<400> SEQUENCE: 26
ccagctgcca gaagaagttc gcccgcagcg ac                                 32

ORAL CANCER VACCINE

TECHNICAL FIELD

The present invention relates to a transformed *Bifidobacterium* capable of expressing and displaying a WT1 protein as an antigen, and to a cancer vaccine using the transformed *Bifidobacterium* as an active ingredient.

The present application is a National Stage Application of PCT/JP2016/065922, filed May 30, 2016, which claims priority from Japanese Patent Application No. 2015-128034, which is incorporated herein by reference.

BACKGROUND ART

The Wilms Tumor 1 (WT1) gene is a gene isolated as a gene responsible for Wilms Tumor, which is a pediatric renal tumor. In Wilms Tumor, deletion or mutation of the gene is found, and transfer of a normal WT1 gene into a cell line derived from Wilms Tumor inhibits cell growth. Accordingly, the WT1 gene has been considered to be a tumor suppressor gene. However, a later investigation has confirmed that a WT1 protein is highly expressed in leukemia and various types of solid tumor, and the WT1 gene is considered to serve a function of an oncogene rather than a tumor suppressor gene (Non Patent Literature 1: Jpn J Clin Oncol 2010; 40: 377-387).

Cancer immunotherapy started with LAK therapy based on innate immunity in the 1980s, and there have been performed: innate immunotherapy, such as NK cell therapy and treatment involving utilizing acquired immunity, such as peptide therapy involving targeting a peptide constituting a fragment of a protein serving as a cancer antigen; and dendritic cell vaccine therapy involving causing dendritic cells to recognize a cancer peptide and returning the cells into the body.

It has been confirmed that, when a mouse is immunized with a WT1 peptide, or when dendritic cells differentiated from human peripheral blood mononuclear cells are stimulated with a WT1 peptide, the WT1 peptide can be utilized as a dendritic cell vaccine capable of inducing WT1-specific cytotoxic T cells (CTLs). In addition, progress has also been made in clinical testing involving using the WT1 peptide. The related-art WT1 peptide is generated so as to be adapted to a certain human leukocyte antigen (HLA), and hence it has been necessary to identify an HLA allele of a patient by DNA typing (Patent Literature 1: JP 5714619 B2). In a later investigation, treatment of cancer using a complete sequence-type vaccine covering a complete sequence of the WT1 protein has been attempted. The vaccine is also applicable to patients of various HLA types. The vaccine also activates cancer antigen-specific CTLs and helper T cells that promote immune responses.

The most general administration route of the WT1 vaccine is subcutaneous or intradermal injection, but attempts have also been made to induce immunity by various administration routes other than the above-mentioned route, for example, transdermal administration and mucosal administration, such as buccal administration, nasal administration, and sublingual administration. However, no report has heretofore been made on oral administration.

A cell membrane is a biological membrane that separates the inside of the cell from the outside. On a surface of the cell membrane, there are a large number of membrane proteins each having a function of providing information on the cell or a function of transporting a substance endogenous or exogenous to the cell. The following concept has been proposed: a certain antigen is fused to a membrane protein so as to be displayed on a cell surface of a microorganism and be used as an oral vaccine for artificially inducing an antigen-antibody reaction. For example, there is known an example in which a vector having a gene encoding a membrane-binding portion of an enzyme protein, such as poly-γ-glutamate synthetase, is utilized to display a target protein on a cell surface of a host microorganism (Patent Literature 2: JP 2005-50054 A). In addition, with regard to a technology involving using, as a vaccine, a flagellin protein derived from a bacterium that causes an infectious disease, there is a report on an oral vaccine containing, as a capsule content, a transformed microorganism expressing flagellin (Patent Literature 3: JP 5187642 B2). In Patent Literature 3, it is reported that the transformed microorganism is prepared using, as the bacterium to be caused to produce flagellin, any of intestinal bacteria that are commonly referred to as good bacteria, such as microorganisms belonging to the genus *Bifidobacterium* (which are collectively referred to as "*Bifidobacterium*") or lactic acid bacteria.

The *Bifidobacterium* is an indigenous bacterium found downstream in the small intestine of a human or other animals, or in the large intestine thereof. The *Bifidobacterium* is an obligately anaerobic Gram-positive bacterium, and hence has high selectivity in culture. Besides, the *Bifidobacterium* has high biocompatibility and does not have endotoxins, which are found in Gram-negative bacteria, and hence the *Bifidobacterium* is highly safe. Therefore, the *Bifidobacterium* has been GRAS-approved according to a standard of a review system regarding food safety. In addition, there is a report that the *Bifidobacterium* has a property of binding to mucus formed of mucin with which the intestinal tract is covered. Accordingly, the *Bifidobacterium* is considered to have a higher property of adhering to the intestinal wall than those of other bacteria in the intestines. There have already been developed and reported a technology for expressing and displaying a protein or a peptide on a surface of such *Bifidobacterium*, and a technology concerning a novel vaccine based on the *Bifidobacterium*, which uses the above-mentioned technology (Patent Literature 4: JP 5561681 B2).

CITATION LIST

Non Patent Literature

[NPL 1] Jpn J Clin Oncol 2010; 40: 377-387

Patent Literature

[PTL 1] JP 5714619 B2
[PTL 2] JP 2005-500054 A
[PTL 3] JP 5187642 B2
[PTL 4] JP 5561681 B2

SUMMARY OF INVENTION

Technical Problem

An object of the present invention is to provide a cancer vaccine that can be orally administered. Another object of the present invention is to provide a cancer vaccine that is not restricted to a certain HLA type.

Solution to Problem

The inventors of the present invention have made extensive investigations, and as a result, have found that a cancer vaccine can be orally administered through the use of a transformed *Bifidobacterium* capable of expressing and displaying a WT1 protein. Thus, the inventors have completed the present invention. The WT1 protein expressed and displayed by the transformed *Bifidobacterium* covers a nearly complete sequence of a WT1 protein unlike a WT1 peptide vaccine restricted to a certain HLA, and the cancer vaccine using the transformed *Bifidobacterium* as an active ingredient is applicable to patients of various HLA types.

That is, the present invention includes the following.

1. A transformed *Bifidobacterium*, including:
DNA encoding a WT1 protein; and
DNA encoding a GNB/LNB substrate-binding membrane protein derived from a *Bifidobacterium*,
the transformed *Bifidobacterium* being designed to display the WT1 protein as an antigen on a surface of the transformed *Bifidobacterium*.

2. A transformed *Bifidobacterium* according to the above-mentioned item 1, in which the WT1 protein is displayed on a cell surface as a fusion protein of the WT1 protein and the GNB/LNB substrate-binding membrane protein (GL-BP-WT1 fusion protein).

3. A transformed *Bifidobacterium* according to the above-mentioned item 1 or 2, in which the WT1 protein includes any one of the following items 1) to 3):

1) a protein identified by an amino acid sequence identified by SEQ ID NO: 1;

2) a protein identified based on an amino acid sequence having one or two or more amino acids substituted, deleted, added, or introduced in the amino acid sequence identified by SEQ ID NO: 1, the protein having immunogenicity as a vaccine; and 3) a protein identified based on an amino acid sequence having 60% or more homology to the amino acid sequence identified by SEQ ID NO: 1, the protein having immunogenicity as a vaccine.

4. A transformed *Bifidobacterium* according to any one of the above-mentioned items 1 to 3, in which the DNA encoding a WT1 protein includes any one of the following items 1) to 4):

1) DNA having a base sequence identified by SEQ ID NO: 2;

2) DNA encoding a protein obtained based on amino acid sequence information identified by SEQ ID NO: 1;

3) DNA capable of hybridizing under stringent conditions with DNA having a base sequence identified by the item 1) or 2); and 4) DNA having a base sequence having 60% or more homology to a base sequence identified by any one of the items 1) to 3).

5. A transformed *Bifidobacterium* according to any one of the above-mentioned items 1 to 4, in which the transformed *Bifidobacterium* includes the DNA encoding a WT1 protein and the DNA encoding a GNB/LNB substrate-binding membrane protein derived from a *Bifidobacterium*.

6. A transformed *Bifidobacterium* according to any one of the above-mentioned items 1 to 5, further including DNA encoding a protein having an adjuvant function between the DNA encoding a WT1 protein and the DNA encoding a GNB/LNB substrate-binding membrane protein derived from a *Bifidobacterium*.

7. A formulation, including the transformed *Bifidobacterium* of any one of the above-mentioned items 1 to 6 as an active ingredient of a vaccine.

8. A formulation according to the above-mentioned item 7, in which the formulation includes a cancer vaccine formulation.

9. A formulation according to the above-mentioned item 8, further including an adjuvant.

10. A formulation according to any one of the above-mentioned items 7 to 9, in which the formulation includes an oral formulation.

11. A method of preventing or treating a cancer, including administering, to a patient, the transformed *Bifidobacterium* of any one of the above-mentioned items 1 to 6 or the formulation of any one of the above-mentioned items 7 to 10.

12. A protein to be displayed on a surface of a *Bifidobacterium*, which is produced from the transformed *Bifidobacterium* of any one of the above-mentioned items 1 to 4.

13. A cancer vaccine, including the protein to be displayed on a surface of a *Bifidobacterium* of the above-mentioned item 12 as an active ingredient.

14. A plasmid or a shuttle vector, including:
DNA encoding a WT1 protein; and
DNA encoding a GNB/LNB substrate-binding membrane protein derived from a *Bifidobacterium*,
the plasmid or the shuttle vector being designed to display the WT1 protein as an antigen on a surface of the *Bifidobacterium*.

Advantageous Effects of Invention

According to the transformed *Bifidobacterium* of the present invention, the WT1 protein can be expressed and displayed on the cell surface of the *Bifidobacterium*. By virtue of displaying a WT1 antigen protein on the surface of the *Bifidobacterium*, the transformed *Bifidobacterium* can be utilized as an oral vaccine effective for a tumor expressing a WT1 protein. The oral vaccine is easy to ingest even for a child or an elderly person, and besides, is free of pain involved in vaccine inoculation by injection. In particular, the oral vaccine of the present invention is highly safe by virtue of the use of the *Bifidobacterium*, which has an experience in food. In addition, the oral vaccine of the present invention is the *Bifidobacterium* capable of expressing a protein covering a nearly complete sequence of a WT1 protein, and hence has low HLA restriction, unlike a WT1 peptide vaccine restricted to a certain HLA. The cancer vaccine using the transformed *Bifidobacterium* as an active ingredient is applicable to patients of various HLA types.

BRIEF DESCRIPTION OF DRAWINGS

FIG. 1 is a conceptual diagram for illustrating a shuttle vector having a WT1 gene downstream of a GL-BP gene, and a GL-BP-WT1 fusion protein expressed on the surface of a *Bifidobacterium* (Example 1).

FIG. 2 is a photographic image for showing results of confirmation of DNA encoding WT1 transferred into a transformed *Bifidobacterium* (Example 1).

FIG. 4 is a diagram for illustrating an experimental protocol for confirming the anti-tumor effect of the transformed *Bifidobacterium* of the present invention through the use of mice (Example 3).

FIG. 5 is a diagram for illustrating an experimental protocol for confirming the anti-tumor effect of the transformed *Bifidobacterium* of the present invention through the use of mice (Example 3).

FIG. 9 is a diagram for illustrating an experimental protocol for confirming the cellular immune response-inducing effect of the transformed *Bifidobacterium* of the present invention through the use of mice (Example 4).

FIG. 10 is a graph for showing results of confirmation of the influence of the administration of the transformed *Bifidobacterium* of the present invention on the body weight of mice (Example 4).

FIG. 15 is a diagram for illustrating an experimental protocol for confirming the anti-tumor effect of the transformed *Bifidobacterium* of the present invention through the use of mice (Example 5).

FIG. 17 is a diagram for illustrating an experimental protocol for confirming the anti-tumor effect of the transformed *Bifidobacterium* of the present invention in combined use with an adjuvant through the use of mice (Example 6).

FIG. 19 is a diagram for illustrating an experimental protocol for confirming the anti-tumor effect of the transformed *Bifidobacterium* of the present invention in combined use with an adjuvant through the use of mice (Example 7).

DESCRIPTION OF EMBODIMENTS (WT1 Protein)

Figure 3A:
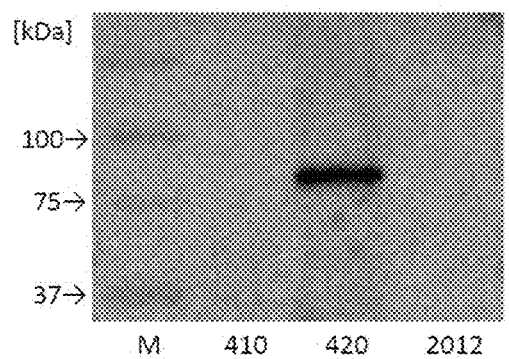
FIGS. 3A and 3B are photographic images for showing: results of confirmation by western blotting of a WT1 protein expressed on the surface of the transformed *Bifidobacterium* of the present invention (FIG. 3A); and results of confirmation thereof by immunofluorescence staining (FIG. 3B) (Example 2).

A WT1 protein is a protein encoded by a WT1 gene, which has been isolated as a gene responsible for Wilms Tumor, which is a pediatric renal tumor. The WT1 protein has been confirmed to have a plurality of T cell epitopes for various HLA types. A WT1 protein of the present invention only needs to contain at least two or more (preferably three or more, more preferably four or more) T cell epitopes, and may be a full-length protein or may be a partial peptide having a deletion at its N-terminus or C-terminus. The full length of the WT1 protein is exemplified below.

```
Full length of WT1 protein GenBank Accession No.
P22561.1 (SEQ ID NO: 22):
MGSDVRDLNALLPAVSSLGGGGGGOGLPVSGARQWAPVLDFAPPGASAYG

SLGGPAPPPAPPPPPPPPHSFIKQEPSWGGAEPHEEQCLSAFTLHFSGQF

TGTAGACRYGPFGPPPPSQASSGQARMFPNAPYLPSCLESQPTIRNQGYS

TVTFDGAPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGM

AAGSSSSVKWTEGQSNHGIGYESENHTAPILCGAQYRIHTHGVFRGIQDV

RRVSGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWHSCQKKFARSDELVRHHNMHQRNMTKLHVAL

Full length of WT1 protein GenBank Accession No.
P19544.2 (SEQ ID NO: 23):
MGSDVRDLNALLPAVPSLGGGGGCALPVSGAAQWAPVLDFAPPGASAYGS

LGGPAPPPAPPPPPPPPHSFIKQEPSWGGAEPHEEQCLSAFTVHFSGQF

TGTAGACRYGPFGPPPPSQASSGQARMFPNAPYLPSCLESQPAIRNQGYS

TVTFDGTPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGV

AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHHNMHQRNMTKLQLAL
```

Herein, the WT1 protein, which serves as an antigen that may be displayed on a *Bifidobacterium* is identified by any one of the following items:

1) a protein identified by an amino acid sequence identified by SEQ ID NO: 1;

2) a protein identified based on an amino acid sequence having one or two or more, for example, one to one hundred twenty, preferably one to sixty, more preferably one to ten, still more preferably one to nine amino acids substituted, deleted, added, or introduced in the amino acid sequence identified by SEQ ID NO: 1, the protein having immunogenicity as a vaccine; and 3) a protein identified based on an amino acid sequence having 60% or more, preferably 80% or more, more preferably 90% or more, still more preferably 95% or more, even still more preferably 97% or more, most preferably 98% or more homology to the amino acid sequence identified by SEQ ID NO: 1, the protein having immunogenicity as a vaccine.

WT1 protein (SEQ ID NO: 1):
PSQASSGQARMFPNAPYLPSCLESQPTIRNQGYSTVTFDGAPSYGHTPSH

HAAQFPNHSFKHEDPMGQQGSLGEQQYSVPPPVYGCHTPTDSCTGSQALL

LRTPYSSDNLYQMTSQLECMTWNQMNLGATLKGMAAGSSSSVKWTEGQSN

HGIGYESENHTAPILCGAQYRIHTHGVFRGIQDVRRVSGVAPTLVRSASE

TSEKRPFMCAYPGCNKRYFKLSHLQMHSRKHTGEKpYQCDFKDCERRFSR

SDQLKRHQRRHTGVKPFQCKTCQRKFSRSDHLKTHTRTHTGKTSEKpFSC

RWHSCQKKFARSDELVRHHNMHQ

T cell epitopes contained in the above-mentioned WT1 protein (SEQ ID NO: 1) are shown in Table 1 below. The WT1 protein of the present invention preferably contains two or more of T cell epitopes corresponding to np332, np126, np187, and np235 shown in Table 1. The WT1 protein contains more preferably three or more, still more preferably all four of the T cell epitopes. Each of those T cell epitopes only needs to be capable of inducing a cellular immune response by being recognized by a T cell, and may have an amino acid sequence having one or two or more, for example, one to five, preferably one to three, more preferably one or two, most preferably one amino acid substituted, deleted, added, or introduced in the amino acid sequence.

Mutant WT1 protein (SEQ ID NO: 16):
PSQASSGQARMFPNAPYLPSCLESQPAIRNQGYSTVTFDGTPSYGHTPSH

HAAQFPNHSFKHEDPMGQQGSLGEQQYSVPPPVYGCHTPTDSCTGSQALL

LRTPYSSDNLYQMTSQLECYTWNQMNLGATLKGVAAGSSSSVKWTEGQSN

HSTGYESDNHTTPILCGAQYRIHTHGVERGIQDVRRVPGVAPTLVRSASE

TSEKRPFMCAYPGCNKRYFKLSHLQMHSRKHTGEKPYQCDFKDCERRFSR

SDQLKRHQRRHTGVKPFQCKTCQRKFSRSDHLKTHTRTHTGKTSEKPFSC

RWPSCQKKFARSDELVRHHNMHQ

Herein, the WT1 protein encompasses an engineered WT1 protein as well. Herein, the engineered WT1 protein refers to a protein obtained by engineering all or part of the amino acids of the WT1 protein identified above through substitution, modification, or the like. The engineered WT1 protein includes a protein having an amino acid sequence having all or part of amino acids, for example, one or two or more, for example, one, two, three, four, five, six, seven, eight, nine, ten, eleven, or twelve amino acids modified in the amino acid sequence identified by the above-mentioned items 1) to 3). Examples of the "modification" of the amino acid that may be present in the engineered WT1 protein include, but not limited to, acetylation, alkylation, such as methylation, glycosylation, hydroxylation, carboxylation, aldehydation, phosphorylation, sulfonylation, formylation, fatty chain addition modification, such as myristoylation, palmitoylation, or stearoylation, octanoylation, esterifica-

TABLE 1

| T cell epitope | Peptide | Amino acid | Sequence | HLA restriction |
|---|---|---|---|---|
| CD4 | np332 | a.a.332-347 | KRYFKLSHLQMHSRKH (SEQ ID NO: 18) | DRB1*0405 |
|  | np126 | a.a.126-134 | RMFPNAPYL (SEQ ID NO: 19) | A0201 |
| CD8 | np187 | a.a.187-195 | SLGEQQYSV (SEQ ID NO: 20) | A0201 |
|  | np235 | a.a.235-243 | CMTWNQMNL (SEQ ID NO: 21) | A0201 A2402 |

In addition, the WT1 protein as used herein also encompasses a WT1 protein identified by the following SEQ ID NO: 14.

WT1 protein (SEQ ID NO: 14):
PSQASSGQARMFPNAPYLPSCLESQPAIRNQGYSTVTFDGTPSYGHTPSH

HAAQFPNHSFKHEDPMGQQGSLGEQQYSVPPPVYGCHTPTDSCTGSQALL

LRTPYSSDNLYQMTSQLECMTWNQMNLGATLKGVAAGSSSSVKWTEGQSN

HSTGYESDNHTTPILCGAQYRIHTHGVFRGIQDVRRVPGVAPTLVRSASE

TSEKRPFMCAYPGCNKRYFKLSHLQMHSRKHTGEKPYQCDFKDCERRFSR

SDQLKRHQRRHTGVKPFQCKTCQRKFSRSDHLKTHTRTHTGKTSEKPFSC

RWPSCQKKFARSDELVRHHNMHQ

In addition, a mutant WT1 protein having an amino acid sequence having a M236Y substitution introduced in an HLA-A*2402-restrictive CTL epitope in the above-mentioned WT1 protein (SEQ ID NO: 14) is shown below. The WT1 protein as used herein also encompasses the following mutant WT1 protein.

tion, amidation, deamidation, disulfide bond formation modification, such as cystine modification, glutathione modification, or thioglycolic acid modification, glycation, ubiquitination, succinimide formation, glutamylation, and prenylation. The engineered WT1 protein may contain one or more amino acid substitutions, deletions, or additions in combination with one or more amino acid modifications.

(*Bifidobacterium*)

The "*Bifidobacterium*" as used herein refers to a microorganism belonging to the genus *Bifidobacterium*. Examples of the *Bifidobacterium* include *Bifidobacterium adolescentis*, *Bifidobacterium angulatum* (*B. angulatum*), *Bifidobacterium animalis* subsp. *animalis* (*B. animalis* subsp. *animalis*), *Bifidobacterium animalis* subsp. *lactis* (*B. animalis* subsp. *lactis*), *Bifidobacterium asteroides* (*B. asteroides*), *Bifidobacterium bifidum* (*B. bifidum*), *Bifidobacterium bourn* (*B. bourn*), *Bifidobacterium breve* (*B. breve*), *Bifidobacterium catenulatum* (*B. catenulatum*), *Bifidobacterium choerinum* (*B. choerinum*), *Bifidobacterium coryneforme* (*B. coryneforme*), *Bifidobacterium cuniculi* (*B. cuniculi*), *Bifidobacterium denticolens* (*B. denticolens*), *Bifidobacterium dentium* (*B. dentium*), *Bifidobacterium gallicum* (*B. gallicum*), *Bifidobacterium gallinarum* (*B. gallinarum*), *Bifidobacterium globosum* (*B. globosum*), *Bifidobacterium indi*- cum (*B. indicum*), *Bifidobacterium infantis* (*B. infantis*), *Bifidobacterium inopinatum* (*B. inopinatum*), *Bifidobacterium lactis* (*B. lactis*), *Bifidobacterium longum* (*B. longum*), *Bifidobacterium magnum* (*B. magnum*), *Bifidobacterium merycicum* (*B. merycicum*), *Bifidobacterium minimum* (*B. minimum*), *Bifidobacterium parvulorum* (*B. parvulorum*), *Bifidobacterium pseudocatenulatum* (*B. pseudocatenulatum*), *Bifidobacterium pseudolongum* subsp. *globosum* (*B. pseudolongum* subsp. *globosum*), *Bifidobacterium pseudolongum* subsp. *pseudolongum* (*B. pseudolongum* subsp. *pseudolongum*), *Bifidobacterium pullorum* (*B. pullorum*), *Bifidobacterium ruminale* (*B. ruminale*), *Bifidobacterium ruminantium* (*B. ruminantium*), *Bifidobacterium saeculare* (*B. saeculare*), *Bifidobacterium scardovii* (*B. scardovii*), *Bifidobacterium subtile* (*B. subtile*), *Bifidobacterium suis* (*B. suis*), *Bifidobacterium thermacidophilum* (*B. thermacidophilum*), and *Bifidobacterium thermophilum* (*B. thermophilum*).

Of those, *Bifidobacterium adolescentis*, *Bifidobacterium animalis* subsp. *animalis* (*B. animalis* subsp. *animalis*), *Bifidobacterium animalis* subsp. *lactis* (*B. animalis* subsp. *lactis*), *Bifidobacterium bifidum* (*B. bifidum*), *Bifidobacterium breve* (*B. breve*), *Bifidobacterium lactis* (*B. lactis*), *Bifidobacterium longum* (*B. longum*), and *Bifidobacterium pseudolongum* subsp. *pseudolongum* (*B. pseudolongum* subsp. *pseudolongum*) are preferably used.

In addition, their resistant strains or mutant strains may be used. Those strains are commercially available or easily available from the depository institution or the like. There are given, for example, *B. longum* JCM1217 (ATCC15707) and *B. bifidum* ATCC11863.

(GNB/LNB Substrate-binding Membrane Protein)

A GNB/LNB substrate-binding membrane protein (GL-BP: galacto-n-biose-lacto-n-biose I-binding protein) is a membrane protein belonging to the ATP binding cassette protein (ABC protein) family, which transports lacto-N-biose (i.e., N-acetyl-3-O-β-D-galactopyranosyl-D-glucosamine) and galacto-N-biose (i.e., N-acetyl-3-O-(β-D-galactopyranosyl)-α-D-galactosamine) of the *Bifidobacterium*. The GNB/LNB substrate-binding membrane protein is hereinafter sometimes referred to simply as "GL-BP". ABC proteins are important membrane proteins that actively transport specific substances on the cell membranes of all organisms through the use of adenosine triphosphate (ATP) as energy, and many kinds of ABC proteins are present on the cell membranes. Accordingly, the GL-BP, which is a kind of ABC protein, is ubiquitously expressed through the utilization of an appropriate promoter in a *Bifidobacterium* having a cellular function for expressing the GL-BP on the surface thereof. Herein, the structure of the GL-BP is not limited to naturally occurring GL-BP, and the GL-BP may have one or more of substitutions, insertions, or deletions in its constituent amino acids as long as the GL-BP has an ability to be expressed on the cell surface of the *Bifidobacterium*.

(Fusion Protein to be displayed on Surface of *Bifidobacterium*)

In the present invention, the WT1 protein to be expressed and displayed on the surface of the *Bifidobacterium* is expressed as a fusion protein with the GL-BP. In the fusion protein, the GL-BP and the WT1 protein are linked in the stated order from the N-terminus. As necessary, the fusion protein may include a protein having an adjuvant function between the GL-BP and the WT1 protein.

(Preparation of Transformed *Bifidobacterium*)

A procedure for preparing the transformed *Bifidobacterium* expressing and displaying the WT1 protein as a fusion protein on the surface of the *Bifidobacterium* is described in order of operations.

1. Acquisition of DNA encoding each Protein

DNA encoding the GL-BP and DNA encoding the WT1 protein may be obtained on the basis of respective known gene information or amino acid sequence information. For example, the DNAs may be acquired by amplifying, through a polymerase chain reaction (PCR), genomic DNA or cDNA prepared from any *Bifidobacterium* serving as a template with the use of a primer pair generated on the basis of genomic information on a structural gene for the GL-BP of the *Bifidobacterium*. In general, a plurality of kinds of genetic codes exist for one amino acid, and hence a gene having a base sequence different from a known base sequence or from a base sequence based on a known amino acid sequence may be adopted. DNA encoding the GL-BP of *B. longum* may be obtained on the basis of, for example, gene information on the GL-BP of *B. longum* identified in Acta Crystallographica Section F., 2007, Volume F63, p. 751. The DNA encoding the GL-BP of *B. longum* may be obtained by amplifying, through PCR, chromosomal DNA or cDNA of *B. longum* serving as a template with the use of a primer pair generated on the basis of gene information. The DNA encoding the WT1 protein may be generated and obtained by a method known per se or any method to be developed in the future on the basis of the amino acid sequence information identified for any of the above-mentioned WT1 proteins. DNAs encoding proteins other than the above-mentioned WT1 proteins may be similarly generated and obtained by a method known per se or any method to be developed in the future.

The DNA encoding each protein described above may be DNA capable of hybridizing under stringent conditions with the DNA acquired as described above. The DNA capable of hybridizing under stringent conditions means DNA obtained by a colony hybridization method, a plaque hybridization method, a Southern blot hybridization method, or the like through the use of the above-mentioned DNA as a probe. A specific example thereof is DNA that can be identified by: performing hybridization at about 65° C. in the presence of sodium chloride at from about 0.7 M to about 1.0 M with a filter having immobilized thereon DNA derived from a colony or a plaque; and then washing the filter with an SSC solution having a concentration of from about 0.1× to about 2× (the composition of an SSC solution having a concentration of 1× is formed of 150 mM sodium chloride and 15 mM sodium citrate) under the condition of about 65° C. A specific example of the DNA capable of hybridizing is DNA having at least about 80% or more homology to the base sequence of the above-mentioned DNA encoding each protein obtained on the basis of known base sequence information or amino acid sequence information, preferably DNA having about 90% or more homology thereto, still more preferably DNA having about 95% or more homology thereto. DNA encoding each protein obtained on the basis of amino acid sequence information may have a different codon as long as an amino acid is encoded.

More specifically, the DNA encoding the WT1 protein is identified by any one of the following items:

1) DNA having a base sequence identified by SEQ ID NO: 2;

2) DNA encoding a protein obtained based on amino acid sequence information identified by SEQ ID NO: 1;

3) DNA capable of hybridizing under stringent conditions with DNA having a base sequence identified by the item 1) or 2); and 4) DNA having a base sequence having 60% or more, preferably 80% or more homology to a base sequence identified by any one of the items 1) to 3).

DNA encoding WT1 protein
(SEQ ID NO: 2)
CTCGAGCCGTCCCAGGCGTCGTCGGGCCAGGCGAGGATGTTCCCGAACGC

GCCCTACCTGCCCAGCTGCCTGGAGTCCCAGCCGACGATCCGCAACCAGG

GCTACTCCACCGTGACGTTCGACGGCGCCCCGTCCTACGGCCACACGCCC

AGCCACCACGCCGCCCAGTTCCCGAACCACAGCTTCAAGCACGAAGACCC

CATGGGCCAGCAGGGCAGCCTCGGCGAACAGCAGTACAGCGTGCCGCCGC

CGGTCTACGGCTGCCACACCCCGACCGACTCCTGCACGGGCTCCCAGGCC

CTGCTCCTGCGTACGCCGTACTCCTCCGACAACCTCTACCAGATGACCTC

CCAGCTGGAGTGCATGACCTGGAACCAGATGAACCTGGGCGCCACGCTGA

AGGGAATGGCCGCGGGGTCGTCGAGCTCCGTCAAGTGGACCGAAGGCCAG

TCCAACCACGGCATCGGCTACGAGTCCGAGAACCACACCGCGCCGATCCT

GTGCGGAGCCCAGTACCGCATCCACACGCACGGCGTCTTCCGCGGCATCC

AGGACGTCCGGCGCGTCTCCGGCGTCGCGCCGACCCTGGTGCGGTCCGCC

TCCGAGACCTCCGAGAAGCGCCCGTTCATGTGCGCCTACCCGGGCTGCAA

CAAGCGCTACTTCAAGCTCTCGCACCTGCAGATGCACTCCCGGAAGCACA

CCGGCGAGAAGCCGTACCAGTGCGACTTCAAGGACTGCGAACGCCGCTTC

TCGCGCAGCGACCAGCTGAAGCGCCACCAGCGTAGGCACACCGGCGTGAA

GCCCTTCCAGTGCAAGACCTGCCAGCGCAAGTTCTCCCGCAGCGACCACC

TCAAGACGCACACCCGCACCCACACCGGCAAGACGTCCGAGAAGCCGTTC

TCGTGCCGCTGGCACAGCTGCCAGAAGAAGTTCGCCCGCAGCGACGAGCT

CGTGCGCCACCACAACATGCACCAGTGAAGCATGC

In addition, the DNA encoding the WT1 protein is, for example, DAN having a base sequence identified by the following SEQ ID NO: 15 or SEQ ID NO: 16.

DNA encoding WT1 protein
(SEQ ID NO: 15)
CCGTCCCAGGCGTCGTCGGGCCAGGCGAGGATGTTCCCGAACGCGCCCTA

CCTGCCCAGCTGCCTGGAGTCCCAGCCGGCGATCCGCAACCAGGGCTACT

CCACCGTGACGTTCGACGGCACCCCGTCCTACGGCCACACGCCCAGCCAC

CACGCCGCCCAGTTCCCGAACCACAGCTTCAAGCACGAAGACCCCATGGG

CCAGCAGGGCAGCCTCGGCGAACAGCAGTACAGCGTGCCGCCGCCGGTCT

ACGGCTGCCACACCCCGACCGACTCCTGCACGGGCTCCCAGGCCCTGCTC

CTGCGTACGCCGTACTCCTCCGACAACCTCTACCAGATGACCTCCCAGCT

GGAGTGCATGACCTGGAACCAGATGAACCTGGGCGCCACGCTGAAGGGAG

TCGCCGCGGGGTCGTCGAGCTCCGTCAAGTGGACCGAAGGCCAGTCCAAC

CACTCCACCGGCTACGAGTCCGACAACCACACCGCCGATCCTGTGCGG

AGCCCAGTACCGCATCCACACGCACGGCGTCTTCCGCGGCATCCAGGACG

TCCGGCGCGTCCCCGGCGTCGCGCCGACCCTGGTGCGGTCCGCCTCCGAG

ACCTCCGAGAAGCGCCCGTTCATGTGCGCCTACCCGGGCTGCAACAAGCG

CTACTTCAAGCTCTCGCACCTGCAGATGCACTCCCGGAAGCACACCGGCG

AGAAGCCGTACCAGTGCGACTTCAAGGACTGCGAACGCCGCTTCTCGCGC

AGCGACCAGCTGAAGCGCCACCAGCGTAGGCACACCGGCGTGAAGCCCTT

CCAGTGCAAGACCTGCCAGCGCAAGTTCTCCCGCAGCGACCACCTCAAGA

CGCACACCCGCACCCACACCGGCAAGACGTCCGAGAAGCCGTTCTCGTGC

CGCTGGCCCAGCTGCCAGAAGAAGTTCGCCCGCAGCGACGAGCTCGTGCG

CCACCACAACATGCACCAGTGAA

DNA encoding WT1 protein
(SEQ ID NO: 17)
CCGTCCCAGGCGTCGTCGGGCCAGGCGAGGATGTTCCCGAACGCGCCCTA

CCTGCCCAGCTGCCTGGAGTCCCAGCCGGCGATCCGCAACCAGGGCTACT

CCACCGTGACGTTCGACGGCACCCCGTCCTACGGCCACACGCCCAGCCAC

CACGCCGCCCAGTTCCCGAACCACAGCTTCAAGCACGAAGACCCCATGGG

CCAGCAGGGCAGCCTCGGCGAACAGCAGTACAGCGTGCCGCCGCCGGTCT

ACGGCTGCCACACCCCGACCGACTCCTGCACGGGCTCCCAGGCCCTGCTC

CTGCGTACGCCGTACTCCTCCGACAACCTCTACCAGATGACCTCCCAGCT

GGAGTGCTACACCTGGAACCAGATGAACCTGGGCGCCACGCTGAAGGGAG

TCGCCGCGGGGTCGTCGAGCTCCGTCAAGTGGACCGAAGGCCAGTCCAAC

CACTCCACCGGCTACGAGTCCGACAACCACACCGCCGATCCTGTGCGG

AGCCCAGTACCGCATCCACACGCACGGCGTCTTCCGCGGCATCCAGGACG

TCCGGCGCGTCCCCGGCGTCGCGCCGACCCTGGTGCGGTCCGCCTCCGAG

ACCTCCGAGAAGCGCCCGTTCATGTGCGCCTACCCGGGCTGCAACAAGCG

CTACTTCAAGCTCTCGCACCTGCAGATGCACTCCCGGAAGCACACCGGCG

AGAAGCCGTACCAGTGCGACTTCAAGGACTGCGAACGCCGCTTCTCGCGC

AGCGACCAGCTGAAGCGCCACCAGCGTAGGCACACCGGCGTGAAGCCCTT

CCAGTGCAAGACCTGCCAGCGCAAGTTCTCCCGCAGCGACCACCTCAAGA

CGCACACCCGCACCCACACCGGCAAGACGTCCGAGAAGCCGTTCTCGTGC

CGCTGGCCCAGCTGCCAGAAGAAGTTCGCCCGCAGCGACGAGCTCGTGCG

CCACCACAACATGCACCAGTGAA

2. Preparation of Vector for transforming *Bifidobacterium*

The preparation of recombinant DNA having the DNAs encoding the respective proteins prepared in the section 1. is described. Herein, for the recombinant DNA, an expression vector or a chromosomal integration vector (e.g., a homologous recombination vector) may be used. A plasmid to be used for the preparation of such vector is not particularly limited as long as the plasmid can be expressed in the *Bifidobacterium*, and the plasmid may be a plasmid known per se or any plasmid to be developed in the future. For example, as a plasmid derived from the *Bifidobacterium*, there may be used pTB6, pBL67, pBL78, pNAL8H, pNAL8M, pNAC1, pBC1, pMB1, pGBL8b, or the like. A composite plasmid of any of those plasmids and a plasmid of *E. coli* may be used. For example, pBLES100, pKKT427, or pRM2 may be used. From the viewpoints of the stability of expression and the ease of preparation of DNA for the preparation of a transformant, of the above-mentioned plasmids, a composite plasmid synthesized from a plasmid of *B. longum* and a plasmid of *E. coli* is suitable.

From the viewpoint of selecting a transformant, it is suitable that the expression vector has a selectable marker, such as antibiotic resistance or an amino acid requirement, on the basis of a method known per se. The expression vector preferably has added thereto a regulatory sequence in order to express the fusion protein of the GL-BP and the WT1 protein, or so as to be advantageous for the expression. Examples of the regulatory sequence include a promoter sequence, a leader sequence, a propeptide sequence, an enhancer sequence, a signal sequence, and a terminator sequence. The origin of each of those regulatory sequences is not particularly limited as long as the regulatory sequence is expressed in the *Bifidobacterium*. The promoter sequence is not particularly limited as long as the promoter sequence is expressed in the *Bifidobacterium*. From the viewpoint of expression efficiency, the promoter sequence of the histone-like protein (HU) of *B. longum*, the LDH promoter thereof, or the like is preferably used. In addition, from the viewpoint of enhancing expression efficiency, the expression vector preferably has a terminator sequence. As the terminator sequence, the terminator sequence of the HU gene is preferably used. In addition, DNA encoding a linker having an appropriate length may be arranged between the DNA encoding the GL-BP and the DNA encoding the WT1 protein.

A cloning vector is prepared by introducing, as necessary, a regulatory sequence, such as a promoter sequence or a terminator sequence, and a selectable marker gene into the above-mentioned plasmid, as described above. Examples of the selectable marker include: antibiotic resistance markers, such as spectinomycin (SPr), ampicillin (Ampr), tetracycline (TETr), kanamycin (KMr), streptomycin (STr), and neomycin (NEOr); fluorescent markers, such as a green fluorescent protein (GFP) and a red fluorescent protein (REP); and enzymes, such as LacZ. The cloning vector preferably has, for example, a linker having a multiple cloning site downstream of its promoter. Through the use of such linker, the DNA encoding the fusion protein is integrated downstream of the promoter and so as to allow in-frame expression of the fusion protein. As the plasmid for the cloning vector, pBLES100, pBLEM100, or the like may be typically used.

In-frame integration of the acquired HU promoter sequence, DNA encoding the GL-BP, and DNA encoding the WT1 protein into the plasmid pBLES100 can generate a vector for expressing the fusion protein on the surface of the *Bifidobacterium*. The expression vector generated by such method is used for the transformation of the *Bifidobacterium*.

3. Preparation of Transformed *Bifidobacterium* expressing Fusion Protein

The recombinant DNA, for example, the expression vector is transferred into the *Bifidobacterium* serving as a host. As a transformation method, a method known per se or any method to be developed in the future may be applied. Specific examples thereof include an electroporation method, a calcium phosphate method, a lipofection method, a calcium ion method, a protoplast method, a microinjection method, and a particle gun method. In the present invention, an electroporation method is preferably used. The electroporation method may be performed under the conditions of from 0.5 kV/cm to 20 kV/cm and from 0.5 μsec to 10 msec. The electroporation method is desirably performed under the conditions of more preferably from 2 kV/cm to 10 kV/cm and from 50 μsec to 5 msec.

The transformant may be selected by using the selectable marker of the fusion protein expression vector as an indicator. As a medium for culturing the transformant, there are given media suited for respective host microorganisms, for example, a glucose blood liver (BL) agar medium, a de Man-Rogosa-Sharpe (MRS) agar medium, a Gifu anaerobic medium (GAM) agar medium, an improved GAM (TGAM) agar medium, a Briggs agar medium, and a yeast extract-glucose-peptone (YGP) agar medium.

The transformant is preferably cultured under anaerobic culture conditions under which the *Bifidobacterium* can be cultured. When the culture is performed under anaerobic conditions, the growth of aerobic bacteria can be prevented. The anaerobic conditions are culture in a hermetic vessel capable of keeping anaerobicity that allows the growth of the *Bifidobacterium*, and examples thereof include conditions that can be established in an anaerobic chamber, an anaerobic box, or the like. A culture temperature only needs to be a temperature at which the *Bifidobacterium* can be cultured, and is generally from 4° C. to 45° C., preferably from 15° C. to 40° C., more preferably from 24° C. to 37° C.

The expression of the fusion protein in the obtained transformed *Bifidobacterium* may be confirmed by a method known per se that is applied in gene recombination technology or any method to be developed in the future. The expression may be confirmed by, for example, a western blotting method. The western blotting method may also be performed by a method known per se. In particular, that the WT1 protein is displayed on the surface of the *Bifidobacterium* can be easily confirmed by subjecting the transformed *Bifidobacterium* to an immunoantibody method involving using, for example, an antibody against the WT1 protein and an FITC-labeled anti-IgG antibody. In the case of expressing a fusion protein of the GL-BP, a protein having an adjuvant function, and the WT1 protein, the protein having an adjuvant function and the WT1 protein are displayed on the surface of the *Bifidobacterium*, and hence the antibody to be used for the confirmation may be an antibody against any of the proteins.

The transformed *Bifidobacterium* that has been confirmed to display the WT1 protein on the surface thereof may be cultured, recovered, and used as it is for the production of a formulation, by methods to be generally used by a person skilled in the art. The obtained *Bifidobacterium* may be inactivated by heat sterilization treatment, radiation irradiation, or the like before use. The transformed *Bifidobacterium* may be subjected to post-treatment by a known method. For example, partial purification may be performed by centrifugation or the like. In addition, as desired, after the partial purification has been performed, the transformed *Bifidobacterium* may be dissolved or suspended in a solvent that has been conventionally used in the art, such as saline, phosphate-buffered saline (PBS), or lactated Ringer's solution. In addition, as desired, the transformed *Bifidobacterium* may be freeze-dried or spray-dried to be formed into a powdery product or a granular product.

(Formulation containing Transformed *Bifidobacterium*)

When it is preferred to administer the WT1 protein displayed on the surface for the purpose of treating or preventing a disease, the transformed *Bifidobacterium* of the present invention may be administered in the form of any formulation. An administration route is not particularly limited, and oral administration or parenteral administration may be performed, but oral administration is suitable because of the purpose of the present invention.

As a formulation suitable for the oral administration, there are given, for example, a tablet, a granule, a fine granule, a powder, a syrup, a solution, a capsule, and a suspension. As a formulation suitable for the parenteral administration, there are given, for example, an injection, an infusion, an inhalation, a spray, a suppository, a transdermal formulation, and a transmucosal formulation.

In the production of a liquid formulation for the oral administration, there may be used formulation additives, for example: water; sugars, such as sucrose, sorbit, and fructose; glycols, such as polyethylene glycol and propylene glycol; oils, such as sesame oil, olive oil, and soybean oil; and preservatives, such as a p-hydroxybenzoic acid ester. In addition, in the production of a solid formulation, such as a capsule, a tablet, a powder, or a granule, there may be used, for example: excipients, such as lactose, glucose, sucrose, and mannite; disintegrants, such as starch and sodium alginate; lubricants, such as magnesium stearate and talc; binders, such as polyvinyl alcohol, hydroxypropyl cellulose, and gelatin; surfactants, such as a fatty acid ester; and plasticizers, such as glycerin.

(Oral Vaccine)

The transformed *Bifidobacterium* displaying the WT1 protein of the present invention can be suitably utilized as an oral vaccine. For example, the WT1 protein is recognized as an antigen on the wall of the intestinal tract, resulting in production of an antibody. Therefore, the transformed *Bifidobacterium* can serve as an effective oral vaccine. For example, each of acid-resistant capsule formulations described below (a seamless capsule formulation, a soft capsule formulation, and a hard capsule formulation), when orally administered, passes through the stomach having a pH of from 1 to 3, without dissolving therein, to reach the intestines, and dissolves in the intestines. The transformed *Bifidobacterium* released from the formulation through the dissolution of the capsule maintains most protein structures even in the intestinal environment and displays the WT1 protein on the surface thereof.

When the transformed *Bifidobacterium* is orally administered, the WT1 protein expressed on the surface of the *Bifidobacterium* is taken up by gut-associated lymphoid tissue (GALT), and is processed with an appropriate epitope by an antigen-presenting cell (APC) in the GALT. Further, it is considered that a peptide subjected to the processing in the GALT is displayed on the APC together with MHC class II or MHC class I, and induces a CTL having a T cell receptor specific to the peptide. It is considered that the APC activates CD8-positive T cells and CD4-positive T cells, and the actions of various cytokines, such as IL-2, released from the CD4-positive T cells, allow the growth of tumor cell-specific CD8-positive T cells (cytotoxic T cells (CTLs)). The WT1 protein of the present invention activates both the CD8-positive T cells and the CD4-positive T cells, and hence is considered to efficiently exhibit an anti-tumor effect on WT1-expressing tumor cells.

In addition, the oral vaccine including the transformed *Bifidobacterium* of the present invention as an active ingredient may include an adjuvant. The adjuvant has an action of boosting the effect of the vaccine. The adjuvant to be used for the oral vaccine of the present invention is preferably an adjuvant capable of boosting the induction of mucosal immunity, and examples thereof include, but not limited to: aluminum hydroxide and inorganic salts thereof; hydrocarbons, such as squalene and oil; bacterial toxins, such as cholera toxin, *E. coli* heat-labile enterotoxin B subunit (LTB), and lipid A from *Salmonella* (MPLA); polysaccharides, such as chitosan and inulin; and combinations thereof.

The present invention relates to a method of preventing or treating a cancer in a subject, including a step of administering the oral vaccine of the present invention to the subject. The dose of the active ingredient varies depending on, for example, the body weight and age of the subject, symptoms, and an administration method, but could be appropriately selected by a person skilled in the art. The cancer to be prevented or treated with the oral vaccine of the present invention may be any tumor in which the WT1 protein can be expressed, and examples thereof include: hematopoietic tumors, such as leukemia, myelodysplastic syndrome, multiple myeloma, and malignant lymphoma; and solid tumor, such as stomach cancer, colorectal cancer, lung cancer, breast cancer, germ cell cancer, liver cancer, skin cancer, bladder cancer, prostate cancer, uterine cancer, cervical cancer, ovarian cancer, and brain cancer.

(Production of Acid-resistant Capsule Formulation containing Transformed *Bifidobacterium*)

The oral vaccine of the present invention preferably has the form of a capsule formulation. Herein, a capsule containing a content is referred to as "capsule formulation". The capsule formulation in the present invention includes a capsule coating and the transformed *Bifidobacterium* expressing the WT1 protein on the surface thereof, and the capsule coating is acid-resistant. The capsule formulation including the acid-resistant capsule coating and the transformed *Bifidobacterium* expressing the WT1 protein on the surface thereof may have any configuration and shape as long as the capsule formulation has the acid-resistant capsule coating and contains, as a capsule content, the transformed *Bifidobacterium* expressing the WT1 protein on the surface thereof. It is not excluded that the capsule formulation includes an additional constituent element. Therefore, the transformed *Bifidobacterium* expressing the WT1 protein on the surface thereof is included or encapsulated in the acid-resistant capsule coating (i.e., contained in the internal region of a capsule formed by the acid-resistant coating). The capsule formulation applicable to the transformed *Bifidobacterium* of the present invention may be produced by a method known per se or any method to be developed in the future.

In order for the transformed *Bifidobacterium* expressing the WT1 protein on the surface thereof to function as an oral vaccine, it is necessary that: the transformed *Bifidobacterium* pass through the stomach to reach the intestines; and the WT1 antigen protein and cell wall proteins of the *Bifidobacterium* be maintained even in the intestines. Incidentally, the pH of the stomach is from 1 to 3, and most proteins of the orally ingested *Bifidobacterium* are denatured owing to the markedly low pH. Therefore, in order that the transformed *Bifidobacterium* to be used in the present invention may reach the human intestines while maintaining various protein structures, and display the WT1 protein, it is preferred that the transformed *Bifidobacterium* be prevented from being affected by gastric acid to the extent possible.

To that end, in the present invention, it is suitable to adopt a capsule formulation in which the transformed *Bifidobacterium* is included or encapsulated in an acid-resistant capsule coating, i.e., the transformed *Bifidobacterium* is contained inside a capsule formed of the acid-resistant coating. The configuration, shape, and the like of the capsule formulation are not particularly limited as long as the coating has resistance to gastric acid. That is, the capsule formulation is desirably configured such that gastric acid is prevented from entering the inside of the capsule to be brought into contact with the transformed *Bifidobacterium*. The capsule coating may be a coating that does not dissolve at a pH of 4 or less, preferably at a pH of from 1 to 3. A capsulation method is also not particularly limited.

EXAMPLES

The present invention is specifically described below by way of Examples. However, the present invention is not limited to Examples below.

Example 1: Generation of *Bifidobacterium* Displaying GL-BP-WT1 on Surface Thereof A. Isolation of GL-BP Gene A GL-BP gene was amplified from *Bifidobacterium longum* JCM1217 (ATCC15707) genome (Accession: EU193949) by performing a PCR reaction using primers glt-f: 5'-ggggtgctgatatattggtttg-3' (SEQ ID NO: 3) and glt-r: 5'-gctcgagctcggaaacagacaggccgaagtt-3' (SEQ ID NO: 4) which allowed the stop codon to be substituted with XhoI, and KOD-Plus-(manufactured by Toyobo Co., Ltd.). PCR products including the amplified GL-BP gene were subjected to agarose gel electrophoresis to excise a 1,989 bp PCR product, and only a GL-BP gene amplification fragment was isolated and purified using Wizard SV Gel and PCR Clean-Up System (manufactured by Promega).

B. Construction of pMW118 Plasmid Having Isolated GL-BP Gene

The isolated and purified GL-BP gene amplification fragment was introduced into the SmaI site of pMW118 having an ampicillin resistance gene (Ampr) (manufactured by Nippon Gene Co., Ltd.) to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed *E. coli* harboring a plasmid having a GL-BP gene. The plasmid was extracted and purified from the transformed *E. coli* using Quantum Prep Plasmid Miniprep Kit (manufactured by Bio-Rad), and its sequence was confirmed by sequencing. Thus, the recombinant plasmid having introduced therein the GL-BP gene was obtained. The obtained recombinant plasmid was named pJT101.

C. Isolation of WT1 Gene

DNA encoding an amino acid sequence from position 117 to position 439 of murine WT1 (SEQ ID NO: 2) was obtained by total synthesis (Funakoshi Co., Ltd.). In the synthesis, codons frequently used in a *Bifidobacterium* were used. In addition, an XhoI recognition sequence (CTCGAG: SEQ ID NO: 5) was added to the N-terminus side, and a stop codon and a succeeding SphI recognition sequence (GCATGC: SEQ ID NO: 6) were added to the C-terminus side. The DNA was introduced into the SmaI site of a pUC18 vector to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed *E. coli* harboring a plasmid having DNA encoding murine WT1 (117 to 439). The plasmid was extracted and purified from the transformed *E. coli* using Quantum Prep Plasmid Miniprep Kit (manufactured by Bio-Rad), and its sequence was confirmed by sequencing. The obtained recombinant plasmid was named pTK2875-1.

Sequence of synthesized murine WT1 gene
(SEQ ID NO: 2)
```
CTCGAGCCGTCCCAGGCGTCGTCGGGCCAGGCGAGGATGTTCCCGAACGC
GCCCTACCTGCCCAGCTGCCTGGAGTCCCAGCCGACGATCCGCAACCAGG
GCTACTCCACCGTGACGTTCGACGGCGCCCCGTCCTACGGCCACACGCCC
AGCCACCACGCCGCCCAGTTCCCGAACCACAGCTTCAAGCACGAAGACCC
CATGGGCCAGCAGGGCAGCCTCGGCGAACAGCAGTACAGCGTGCCGCCGC
CGGTCTACGGCTGCCACACCCCGACCGACTCCTGCACGGGCTCCCAGGCC
CTGCTCCTGCGTACGCCGTACTCCTCCGACAACCTCTACCAGATGACCTC
CCAGCTGGAGTGCATGACCTGGAACCAGATGAACCTGGGCGCCACGCTGA
AGGGAATGGCCGCGGGGTCGTCGAGCTCCGTCAAGTGGACCGAAGGCCAG
TCCAACCACGGCATCGGCTACGAGTCCGAGAACCACACCGCGCCGATCCT
GTGCGGAGCCCAGTACCGCCATCCACACGCACGGCGTCTTCCGCGGCATCC
AGGACGTCCGGCGCGTCTCCGGCGTCGCGCCGACCCTGGTGCGGTCCGCC
TCCGAGACCTCCGAGAAGCGCCCGTTCATGTGCGCCTACCCGGGCTGCAA
CAAGCGCTACTTCAAGCTCTCGCACCTGCAGATGCACTCCCGGAAGCACA
CCGGCGAGAAGCCGTACCAGTGCGACTTCAAGGACTGCGAACGCCGCTTC
TCGCGCAGCGACCAGCTGAAGCGCCACCAGCGTAGGCACACCGGCGTGAA
GCCCTTCCAGTGCAAGACCTGCCAGCGCAAGTTCTCCCGCAGCGACCACC
TCAAGACGCACACCCGCACCCACACCGGCAAGACGTCCGAGAAGCCGTTC
TCGTGCCGCTGGCACAGCTGCCAGAAGAAGTTCGCCCGCAGCGACGAGCT
CGTGCGCCACCACAACATGCACCAGTGAAGCATGC
```

A plasmid having DNA encoding an amino acid sequence from position 117 to position 350 of murine WT1 was generated as described below. That is, with the use of the pTK2875 obtained above as a template, a PCR reaction was performed using a primer WT1-f (5'-CGCTCGAGCCGTC-CCAGGCGTCGT-3': SEQ ID NO: 7) and a primer WT1-r2 (5'-GCGCATGCTCACTCGCCGGTGTGCTTCCGG-3': SEQ ID NO: 8), and KOD-Plus-(manufactured by Toyobo Co., Ltd.), to amplify a DNA fragment encoding murine WT1 (117 to 350). A stop codon and a succeeding SphI recognition sequence (GCATGC: SEQ ID NO: 6) were added to the C-terminus side. The amplified PCR products were subjected to agarose gel electrophoresis to excise a 721 bp PCR product, which was isolated and purified using Wizard SV Gel and PCR Clean-Up System (manufactured by Promega). The isolated and purified product was introduced into the SmaI site of a pUC18 vector to construct a plasmid. DNA Ligation Kit Ver. 2 (manufactured by Takara Bio Inc.) was used for ligation. The constructed plasmid was transferred into *E. coli* DH5a (manufactured by Takara Bio Inc.) by a heat shock method (42° C., 30 seconds). The resultant was applied to an LB agar medium containing 100 µg/ml of ampicillin (manufactured by Difco), and was cultured at 37° C. overnight to provide transformed *E. coli* harboring a plasmid having DNA encoding murine WT1 (117 to 350). The plasmid was extracted and purified from the transformed *E. coli* using Quantum Prep Plasmid Miniprep Kit (manufactured by Bio-Rad), and its sequence was confirmed by sequencing. The obtained recombinant plasmid was named pTK2875-2.

D. Construction of Plasmid having WT1 Gene Downstream of GL-BP Gene

The plasmids pTK2875-1 and pTK2875-2 each harboring the WT1 gene obtained in the section C. were treated with restriction enzymes XhoI and SphI and subjected to agarose gel electrophoresis to excise 986 bp and 718 bp DNA fragments, respectively, which were isolated and purified using Wizard SV Gel and PCR Clean-Up System (manufactured by Promega). Those WT1 gene amplification fragments were introduced into the above-mentioned pJT101 plasmids, which had also been treated with restriction enzymes XhoI and SphI, respectively, using DNA Ligation Kit Ver. 2, to construct plasmids. Each of the constructed plasmids was transferred into *E. coli* DH5a by a heat shock method. The resultant was applied to an LB agar medium containing 100 µg/ml of ampicillin, and was cultured at 37° C. overnight to provide transformed *E. coli* harboring a plasmid having a fusion gene of the GL-BP gene and the WT1 gene (FIG. 1). The plasmid was extracted and purified from the obtained transformed *E. coli* using Quantum Prep Plasmid Miniprep Kit, and its sequence was confirmed by sequencing. Thus, a recombinant plasmid having the WT1 gene linked downstream of the GL-BP gene was obtained. The obtained recombinant plasmids were named pTK2895 (GLBP-WT1 (117 to 439)) and pTK2896 (GLBP-WT1 (117 to 350)), respectively.

E. Construction of *E. coli-Bifidobacterium* Shuttle Vector

As an *E. coli-Bifidobacterium* shuttle vector, the *E. coli-Bifidobacterium* shuttle vector pJW241 disclosed in Vaccine. 28:6684-6691 (2010) was used.

F. Integration of Gene Having GL-BP Gene and WT1 Gene Linked to Each Other into *E. coli-Bifidobacterium* Shuttle Vector pJW241

With the use of each of the vectors pTK2895 (GLBP-WT1 (117 to 439)) and pTK2896 (GLBP-WT1 (117 to 350)) each having the fusion gene having the GL-BP gene and the WT1 gene linked to each other (hereinafter referred to as "this fusion gene") as a template, PCR was performed using a primer Infusion-F (5'-ggaaaactgtccatagatggcgaggcgaacgc-cacg-3': SEQ ID NO: 9) and a primer Infusion-R (5'-tttcatctgtgcatagtgctgcaaggcgattaagtt-3': SEQ ID NO: 10). The PCR amplified products were subjected to agarose gel electrophoresis to excise this fusion gene, which was isolated and purified using Wizard SV Gel and PCR Clean-Up System (manufactured by Promega). In addition, separately from the foregoing, the *E. coli-Bifidobacterium* shuttle vector pJW241 (Vaccine. 28:6684-6691 (2010)) was treated with restriction enzyme NdeI. This fusion gene that had been purified and the pJW241 were each ligated using In-Fusion HD Cloning Kit (manufactured by Clontech), and the obtained plasmid was transferred into *E. coli* DH5a by a heat shock method. The resultant was applied to an LB agar medium containing 70 µg/ml of spectinomycin, and was cultured at 37° C. overnight to provide transformed *E. coli* harboring a plasmid having the origin of replication, i.e., ori region of *E. coli*, a spectinomycin resistance gene (SPr), the origin of replication, i.e., ori region of *Bifidobacterium*, and this fusion gene. The plasmid was extracted and purified from the transformed *E. coli* using Quantum Prep Plasmid Miniprep Kit, and the presence of the sequence of this fusion gene was confirmed. The obtained recombinant plasmids were named pTK2897 (GLBP-WT1 (aa 117 to 439)) and pTK2898 (GLBP-WT1 (aa 117 to 350)), respectively.

G. Preparation of Host *Bifidobacterium* Liquid

*Bifidobacterium longum* 105-A (Matsumura H. et al., Biosci. Biotech. Biochem., 1997, vol. 61, pp. 1211-1212: donated by Tomotari Mitsuoka, a professor emeritus at the University of Tokyo) was inoculated on 50 ml of a GAM medium (manufactured by Nissui Pharmaceutical Co., Ltd.), and was cultured at 37° C. using AnaeroPack™ Kenki (manufactured by Mitsubishi Gas Chemical Company, Inc.). During the culture, an absorbance at a wavelength of 600 nm was measured, and the culture was terminated when the absorbance reached from 0.4 to 0.8. After the completion of the culture, centrifugation (6,000×g, for 10 minutes) was performed with a high-speed centrifuge to collect the bacterial cells. The collected bacterial cells were washed two or three times by adding 10 ml of a 10% (v/v) glycerol solution to suspend the bacterial cells and centrifuging the suspension with a high-speed centrifuge.

H. Generation of *Bifidobacterium* Displaying GL-BP-WT1 Fusion Protein on Surface Thereof by Transformation of *Bifidobacterium* with Recombinant Plasmids pTK2897 and pTK2898

The host *Bifidobacterium* liquid obtained in the section G. was suspended by adding 500 µl of a 10% (v/v) glycerol solution thereto. 200 µl of the suspension was taken in a separate tube, and 5 µl of each of solutions respectively containing the recombinant plasmids pTK2897 and pTK2898 obtained in the section F. was added. The contents were mixed, and the whole was left to stand on ice for 5 minutes. Then, the mixed liquid was placed in a 0.2 cm electroporation cuvette (manufactured by Bio-Rad) and subjected to electroporation using a Gene Pulser Xcell electroporation system (manufactured by Bio-Rad) under the conditions of 2 kV, 2.5 µF, and 200Ω. Immediately after the electroporation, 0.8 ml of a GAM medium that had been adjusted to 37° C. in advance was added, and the cells were cultured at 37° C. for 3 hours using AnaeroPack™ Kenki. Then, the resultant was applied to a GAM agar medium containing 70 µg/ml of spectinomycin (manufactured by Nissui Pharmaceutical Co., Ltd.), and was cultured at 37° C. using AnaeroPack™ Kenki to provide transformed *Bifidobacterium*. The obtained transformed *Bifidobacterium* was inoculated on a GAM medium containing 70 µg/ml of spectinomycin, and was cultured at 37° C. using AnaeroPack™ Kenki. After the completion of the culture, the culture broth was dispensed into a 1.5 ml tube and suspended by adding an equal amount of a 50% (v/v) glycerol solution. The resultant suspension was stored at −80° C. to generate a frozen stock, and the frozen stock was used as master cells of *Bifidobacterium* displaying a GL-BP-WT1 fusion protein on the surface thereof (sometimes referred to as "transformed *Bifidobacterium*") (TK2900 (GLBP-WT1 (aa 117 to 439)) and TK2903 (GLBP-WT1 (aa 117 to 350)), respectively).

FIG. 2 is an image for showing results of confirmation by electrophoresis of the lengths of amplified fragments obtained by amplifying the gene (DNA) of each recombinant *Bifidobacterium* by PCR using the following primers.

```
Forward primer 410, 420:
                                 (SEQ ID NO: 11)
ACGATCCGCAACCAGGGCTACTC Reverse primer 410:
                                 (SEQ ID NO: 12)
ggtgcgagagcttgaagtagcgc Reverse primer 420:
                                 (SEQ ID NO: 13)
gtcgctgcgggcgaacttcttc
```

410 represents *B. longum* 410, which is a *Bifidobacterium* transformed with a shuttle vector having inserted therein DNA encoding murine WT1 (aa 170 to 350) and corresponds to the TK2903 (GLBP-WT1 (aa 117 to 350)). 420 represents B. longum 420, which is a Bifidobacterium transformed with a shuttle vector having inserted therein DNA encoding murine WT1 (aa 117 to 439) and corresponds to the TK2900 (GLBP-WT1 (aa 117 to 439)). 2012 represents B. longum 2012, which is a Bifidobacterium transformed with a shuttle vector having inserted therein only a GLBP gene without having inserted therein DNA encoding murine WT1. The primers denoted by 410 amplify the DNA encoding murine WT1 (aa 117 to 350), and the primers denoted by 420 amplify the DNA encoding murine WT1 (aa 117 to 439).

It was confirmed from the results of FIG. 2 that the DNA encoding WT1 was certainly transferred into each recombinant Bifidobacterium.

Example 2: Confirmation of Displaying of GL-BP-WT1 Fusion Protein of Transformed Bifidobacterium on Surface Thereof (1) Each transformed Bifidobacterium obtained in Example 1 described above was centrifuged with a high-speed centrifuge to collect the bacterial cells. The collected bacterial cells were washed three times by adding PBS thereto to suspend the bacterial cells and centrifuging the suspension with a high-speed centrifuge. To the bacterial cells, a solution containing PBS, 1 M Tris-HCl (pH 8.0) (manufactured by Nippon Gene Co., Ltd.), and Triton X-100 (manufactured by Wako Pure Chemical Industries, Ltd.) was added, and the whole was left to stand on ice for 30 minutes. To the resultant solution, an equal amount of a 2×SDS gel electrophoresis buffer was added, and the whole was left to stand at 95° C. for 5 minutes to provide a sample for electrophoresis. Then, 8% (w/v) acrylamide gel was set in an electrophoresis apparatus (manufactured by ATTO Corporation), and the obtained sample was applied and subjected to electrophoresis along with a molecular weight marker at a current of 20 mA for 1.5 hours. The gel after the electrophoresis was placed on a nitrocellulose membrane (manufactured by ATTO Corporation) and subjected to blotting with a blotting apparatus (manufactured by Bio-Rad) by applying a current of 20 mA thereto. After the blotting, the nitrocellulose membrane was subjected to blocking by being immersed in TBS (manufactured by Nippon Gene Co., Ltd.) serving as a buffer containing 4% (w/v) skim milk (manufactured by BD) for 1 hour. After the blocking, the nitrocellulose membrane was washed twice with TBS. After the washing, the nitrocellulose membrane was immersed in TBS supplemented with a 0.5% (w/v) primary antibody (WT1 antibody (C-19): sc-192: manufactured by Santa Cruz Biotechnology) for 1.5 hours, and was washed three times with TBS. Then, the nitrocellulose membrane was immersed in TBS supplemented with a 0.5% (w/v) secondary antibody (goat anti-rabbit IgG-HRP: sc-2004: manufactured by Santa Cruz Biotechnology) for 3 hours. Then, the nitrocellulose membrane was washed three times with TBS, allowed to develop a color using a 1-Steptm NBT/BCIP plus Suppressor kit (manufactured by Pierce) for 30 minutes under a light-shielding condition, and rinsed with pure water. After that, the surface expression of the GL-BP-WT1 fusion protein was confirmed on the basis of the developed color.

The results of the western blotting are shown in FIG. 3A. As apparent from FIG. 3A, B. longum 420 showed a clear band at 82.9 kDa corresponding to the sum of the molecular weights of WT1 (aa 117 to 439) and the GL-BP fusion protein. Therefore, it was confirmed that the transformed Bifidobacterium (B. longum 420) expressed the GL-BP-WT1 fusion protein.

(2) Each transformed Bifidobacterium obtained in Example 1 described above that had been cultured was centrifuged with a high-speed centrifuge to collect the bacterial cells. The collected bacterial cells were washed three times by adding PBS (manufactured by Nippon Gene Co., Ltd.) serving as a buffer thereto to suspend the bacterial cells and centrifuging the suspension with a high-speed centrifuge. Then, PBS containing 1% (w/v) BSA supplemented with a primary antibody (WT1 antibody (C-19): sc-192: manufactured by Santa Cruz Biotechnology) was added to the Bifidobacterium liquid to suspend the cells, and the suspension was left to stand at 37° C. for 30 minutes. The bacterial liquid that had been left to stand for 30 minutes was centrifuged with a high-speed centrifuge to collect the bacterial cells. The collected bacterial cells were washed twice by adding PBS thereto to suspend the bacterial cells and centrifuging the suspension with a high-speed centrifuge. Then, PBS containing 1% (w/v) BSA supplemented with a secondary antibody Alexa Fluor™ 488 Rabbit Anti-Mouse IgG antibody (manufactured by Molecular Probes) was added to the Bifidobacterium liquid to suspend the cells, and the suspension was left to stand at 37° C. for 30 minutes. The bacterial liquid that had been left to stand for 30 minutes was centrifuged with a high-speed centrifuge to collect the bacterial cells. The collected bacterial cells were washed twice by adding PBS thereto to suspend the bacterial cells and centrifuging the suspension with a high-speed centrifuge, and were then observed with a fluorescence microscope (manufactured by Keyence Corporation).

Figure 3B:
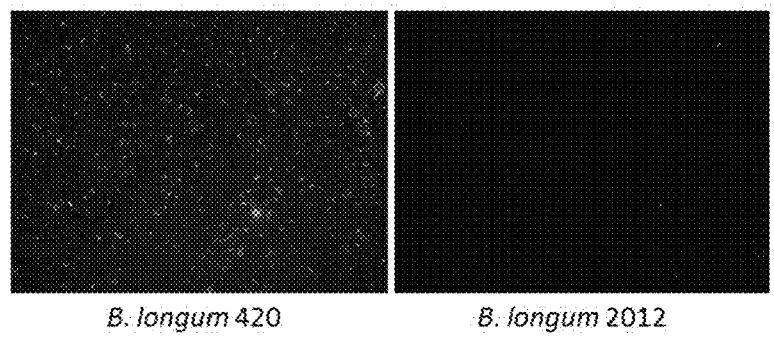

The results of the observation with the fluorescence microscope are shown in FIG. 3B. The left-hand side of FIG. 3B is a fluorescence micrograph of B. longum 420, which is a transformed Bifidobacterium obtained in Example 1 described above, and the right-hand side of FIG. 3B is a fluorescence micrograph of B. longum 2012. It was confirmed from the fluorescence micrographs that WT1 was present on the cell surface of B. longum 420.

Example 3: Confirmation of Anti-Tumor Effect of Oral Administration of GL-BP-WT1 Fusion Protein of Transformed Bifidobacterium An anti-tumor effect achieved when the frozen stock of each transformed Bifidobacterium obtained in Example 1 described above was orally administered to mice was confirmed. An experimental protocol is illustrated in FIG. 4 and FIG. 5.

Murine WT1-expressing C1498 cells (murine leukemia cells) were subcutaneously transplanted into the right flank of C57BL/6 (female, 6- to 8-week-old). The cells were transplanted at $1 \times 10^6$ cells/200 µl of RPMI1640 and Matrigel per mouse, and the day of the transplantation was defined as Day 0. The size of a tumor was confirmed every 4 days.

Figure 6A:
FIGS. 6A-6C are photographic images for showing results of confirmation of the anti-tumor effect of the transformed *Bifidobacterium* of the present invention (Example 3).
Figure 6B:
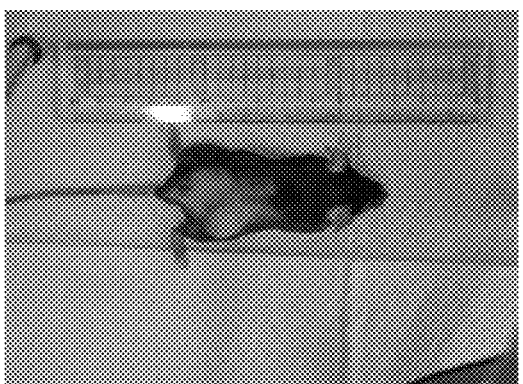
Figure 6C:
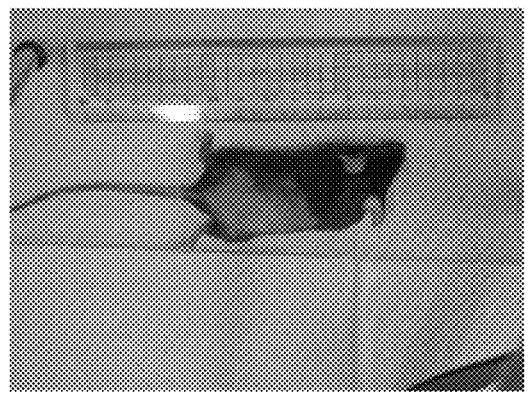

Photographs of typical subcutaneous tumors on the 19th day after the tumor inoculation (Day 19) are shown in FIGS. 6A-6C.

Figure 7:
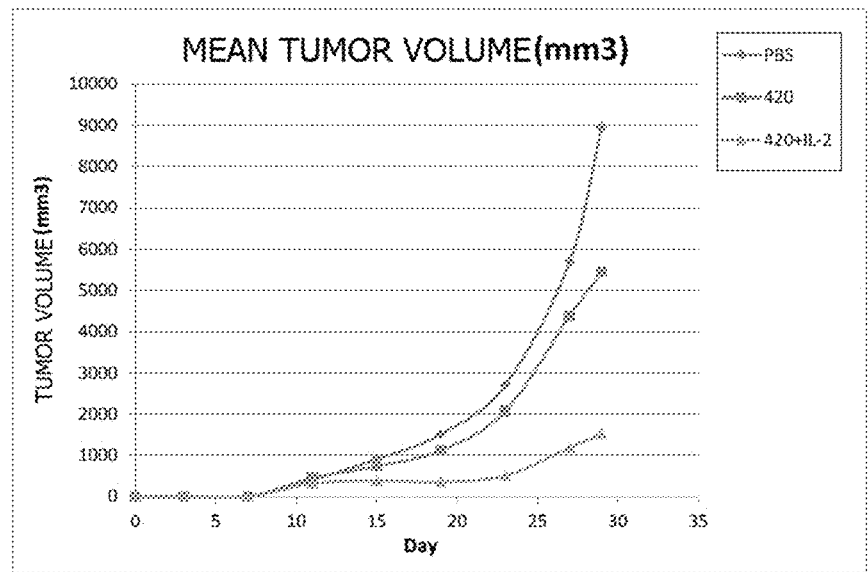
FIG. 7 is a graph for showing results of confirmation over time of the anti-tumor effect of the transformed *Bifidobacterium* of the present invention (Example 3).
Figure 8:
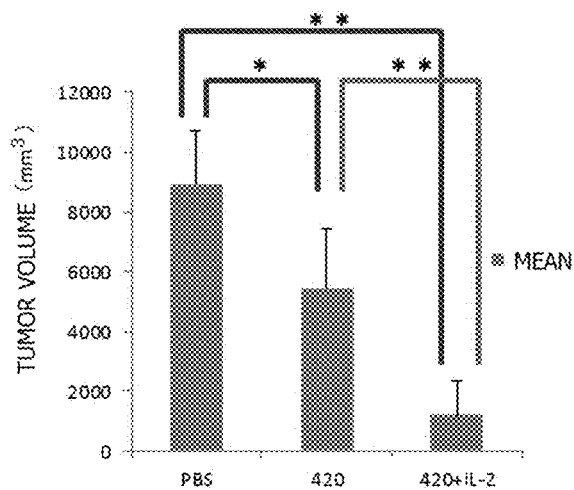
FIG. 8 is a graph for showing results of confirmation of the anti-tumor effect of the transformed *Bifidobacterium* of the present invention (Example 3).

In addition, changes over days in tumor size are shown in FIG. 7, and the sizes of the tumors on the 29th day after the tumor inoculation (Day 29) are shown in FIG. 8. It was found that tumor growth was able to be significantly inhibited in the group administered with B. longum 420 alone as compared to that in the PBS-administered group (*: $p<0.05$, **: $p<0.001$). In addition, it was found that, through the combined use of B. longum 420 and IL-2, tumor growth was able to be significantly inhibited on Day 19 and thereafter as compared to that in the PBS-administered group (p<0.01), and tumor growth was able to be significantly inhibited on Day 29 as compared to that in the group administered with *B. longum* 420 alone (p<0.01). The combined use with IL-2 boosted the anti-tumor effect of *B. longum* 420.

Example 4: Confirmation of Cellular Immune Response-inducing Effect of Oral Administration of GL-BP-WT1 Fusion Protein of Transformed *Bifidobacterium*

A cellular immune response-inducing effect achieved when the frozen stock of each transformed *Bifidobacterium* obtained in Example 1 described above was orally administered to mice was confirmed. An experimental protocol is illustrated in FIG. 9. During the observation period from Day 0 to Day 29, the mean body weight of the *B. longum* 420-administered group changed similarly to those in the other groups (FIG. 10), and side effects, such as diarrhea and a behavioral defect, of the administration of *B. longum* 420 were not observed.

(1) On Day 27, the spleen was collected from each of the mice to prepare splenocytes. The splenocytes were cultured, and the concentrations of various cytokines of the cellular immune system in the splenocyte culture supernatant were measured. A C1498 murine leukemia cell line having a murine WT1 gene transferred thereinto so as to express a murine WT1 protein (C1498-WT1 cells) was used as an antigen for stimulating the splenocytes, and C1498 cells having transferred thereinto an empty vector not having inserted therein the murine WT1 gene (C1498-Mock cells) were used as a control.

$4 \times 10^5$ cells/well of the murine splenocytes were subjected to stimulated culture with mitomycin C-treated C1498-WT1 cells or C1498-Mock cells ($4 \times 10^4$ cells/well in each case) in a 96-well plate at 37° C. for 3 days (n=5). After the culture, the cell culture broth was recovered, and the concentrations of various cytokines (interferon-γ (IFN-γ), interleukin-2 (IL-2), and tumor necrosis factor α (TNF-α)) were measured by an enzyme-linked immuno sorbent assay (ELISA) method. The measurement of the concentrations of the various cytokines was performed using Mouse IFN-gamma Quantikine ELISA Kit (R&D Systems, Minneapolis, Minn.), Mouse TNF-alpha Quantikine (R&D Systems), and Mouse IL-2 ELISA Kit (Thermo Scientific, Waltham, Mass.) by methods in conformity to the manuals of the kits.

Figure 11A:
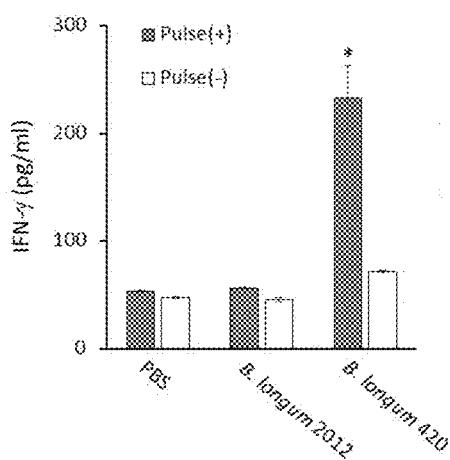
FIGS. 11A-11C are graphs for showing results of confirmation of the influence of the transformed *Bifidobacterium* of the present invention on cytokine production capacity (Example 4).
Figure 11B:
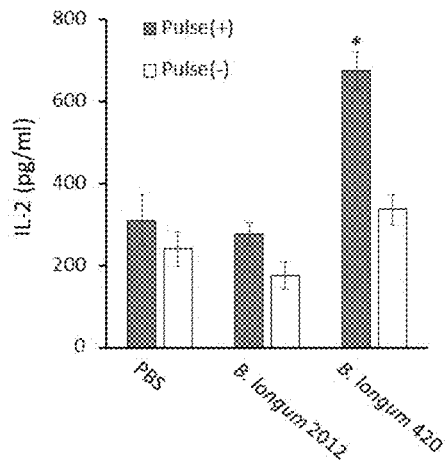
Figure 11C:
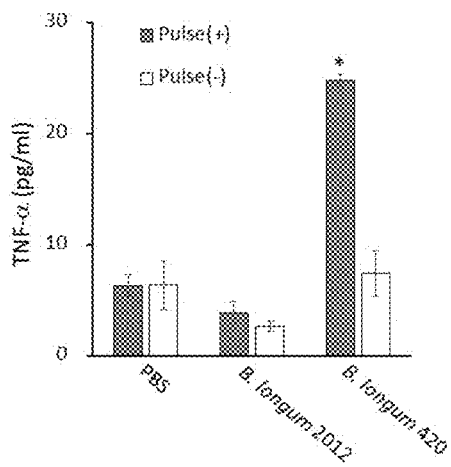
Figure 12A:
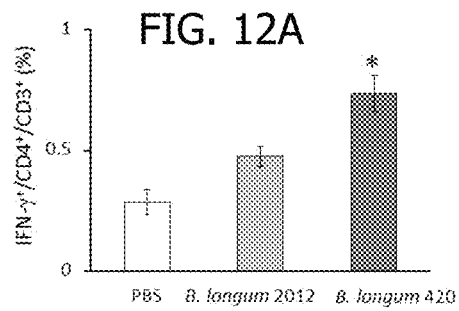
FIGS. 12A-12F are graphs for showing results of confirmation of the influence of the transformed *Bifidobacterium* of the present invention on activated T cell induction capacity (Example 4).
Figure 12B:
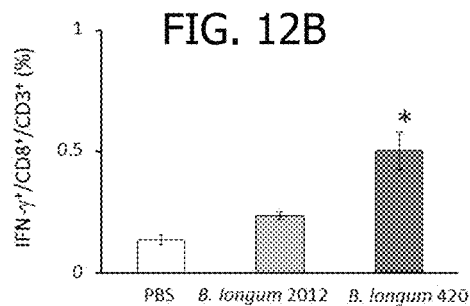
Figure 12C:
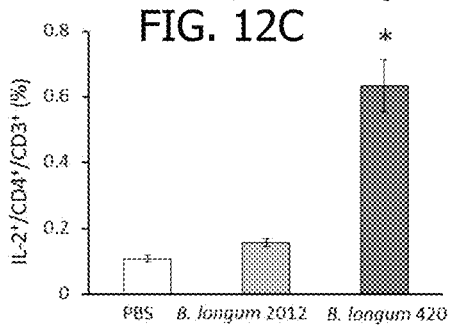
Figure 12D:
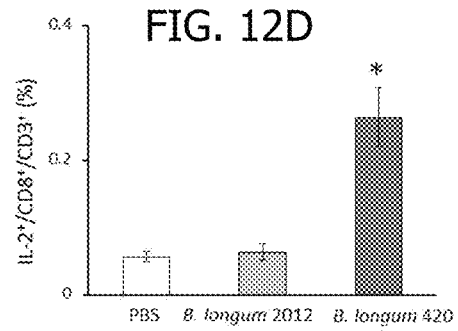
Figure 12E:
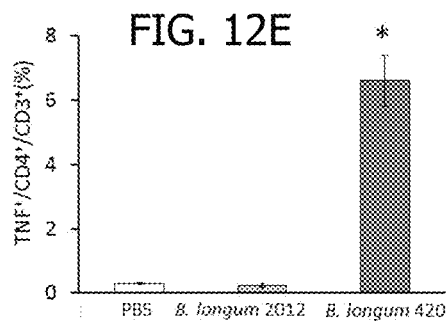
Figure 12F:
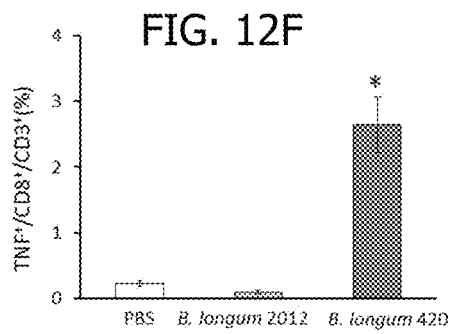

The results are shown in FIGS. 11A-11C. In the *B. longum* 420-administered group, the production amounts of IFN-γ, IL-2, and TNF-α were significantly increased by restimulation with the C1498-WT1 cells as compared to those in the non-stimulated group (*: p<0.01). The production amount of IFN-γ in the *B. longum* 420-administered group was significantly increased as compared to those in the PBS-administered group and the *B. longum* 2012-administered group (*: p<0.01). Therefore, it was shown that, as a result of the oral administration of the GL-BP-WT1 fusion protein of the transformed *Bifidobacterium*, the production of various cytokines important for WT1-specific anti-tumor immunity was boosted by stimulation with the WT1 protein.

(2) Splenocytes prepared in the same manner as in the section (1) were subjected to intracellular cytokine staining (ICCS) to confirm the ratio of cytokine-producing T cells in CD4-positive T cells or CD8-positive T cells.

The murine splenocytes ($2 \times 10^6$ cells/well, n=5) were mixed with $2 \times 10^5$ cells/well of the C1498-WT1 cells, and the cells were cultured in a 24-well plate under the conditions of 37° C. and 5% $CO_2$ for 42 hours. At this time, GolgiStop or GolgiPlug (BD) was added to each well, and the cells were further cultured for 6 hours. The cells were recovered, and subjected to intracellular cytokine staining using BD/Cytofix/Cytoperm Plus Fixation/Permeabilization Kit (BD). An FITC-labeled anti-CD3 monoclonal antibody, an FITC-labeled anti-CD8 monoclonal antibody, or an FITC-labeled anti-CD4 monoclonal antibody was added, followed by mixing. The cells were washed with a buffer for staining. Various anti-cytokine antibodies were added to the cells, and the cells were gently suspended. After that, the whole was left to stand still in a dark place at room temperature. The cells were washed, and then resuspended in a buffer for staining. After that, the cells were analyzed with a flow cytometer using analysis software included therewith. A specific method performed was in conformity to the manual of the kit.

The results are shown in FIGS. 12A-12F. In the *B. longum* 420-administered group, both the CD4+T cells and CD8+T cells that produced IFN-γ, IL-2, and TNF in the splenocytes significantly increased as compared to those in the other administered groups (*: p<0.05). Therefore, it was shown that the oral administration of the GL-BP-WT1 fusion protein of the transformed *Bifidobacterium* increased the CD4$^+$T cells and CD8$^+$T cells that produced cytokines involved in WT1-specific cellular immunity.

(3) For splenocytes prepared in the same manner as in the section (1), the ratio of WT1 (Db126 peptide)-specific CD8$^+$T cells in CD8-positive T cells was confirmed using a WT1 tetramer.

$2 \times 10^6$ cells/well of the murine splenocytes (n=5) were mixed with $2 \times 10^5$ cells/well of the C1498-WT1 cells, and the cells were cultured in a 24-well plate under the conditions of 37° C. and 5% $CO_2$ for 7 days. On the 1st day and the 3rd day of the culture, 20 IU/ml of IL-2 was added to induce CTLs. After the culture, CD8-positive T cells were detected using an FITC-labeled anti-CD3 monoclonal antibody and an FITC-labeled anti-CD8 monoclonal antibody, and WT1 peptide-specific CD8$^+$T cells (CTLs) were detected using H-2Db WT1 Tetramer-RMFPNAPYL (MBL). The cells were analyzed with a flow cytometer using analysis software included therewith.

Figure 13:
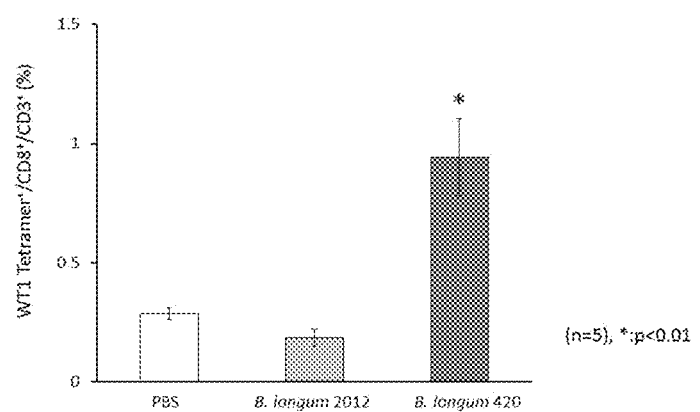
FIG. 13 is a graph for showing results of confirmation of the WT1-specific CTL induction capacity of the transformed *Bifidobacterium* of the present invention (Example 4).

The results are shown in FIG. 13. When the transformed *Bifidobacterium* is orally administered, the GL-BP-WT1 fusion protein expressed on the surface of the *Bifidobacterium* is taken up by gut-associated lymphoid tissue (GALT) and processed with an appropriate epitope by an antigen-presenting cell (APC) in the GALT. Further, it is considered that a peptide subjected to the processing in the GALT is displayed on the APC together with MHC class II to induce a CTL having a T cell receptor specific to the peptide. H-2Db WT1 Tetramer-RMFPNAPYL binds to a T cell receptor specific to a CD8 epitope (a.a. 126-134: RMFPNAPYL (SEQ ID NO: 19)), which is one of the epitopes contained in the WT1 protein, to emit fluorescence, and hence enables the confirmation of the induction of the CTL specific to the CD8 epitope. It was found from the results of FIG. 13 that the ratio of WT1 tetramer-positive CTLs in the splenocytes in the *B. longum* 420-administered group significantly increased as compared to those in the other administered groups (*; p<0.05). Therefore, it was shown that the GL-BP-WT1 fusion protein of the orally administered transformed *Bifidobacterium* was appropriately processed to induce WT1 peptide-specific CTLs playing an important role in anti-tumor effect.

(4) For splenocytes prepared in the same manner as in the section (1), the activity of WT1-specific cytotoxic T cells (CTLs) was measured.

3×10$^7$ cells/well of the murine splenocytes (n=5) were mixed with 3×10$^6$ cells/well of the C1498-WT1 cells, and the cells were cultured in a 6-well plate under the conditions of 37° C. and 5% CO$_2$ for 6 days. On the 1st day and the 3rd day of the culture, 20 IU/ml of IL-2 was added to induce CTLs. The splenocytes were recovered. In a 96-well plate, the splenocytes were mixed with 1×10$^4$ cells/well of the C1498-WT1 cells or the C1498-Mock cells at a ratio of 20:1, 10:1, or 5:1, and then the cells were cultured under the conditions of 37° C. and 5% CO$_2$ for 8 hours. The culture supernatant was recovered, and lactate dehydrogenase activity in the culture supernatant was measured using Cytotox 96 Non-radioactive Citotoxicity Assay Kit (Promega). On the basis of the measured activity, cytotoxic activity was calculated. Lactate dehydrogenase is an enzyme present in the cytoplasm. Lactate dehydrogenase normally does not permeate the cell membrane, but is released into the medium when the cell membrane is injured. Therefore, lactate dehydrogenase is used as an indicator for cytotoxic activity.

Figure 14A:
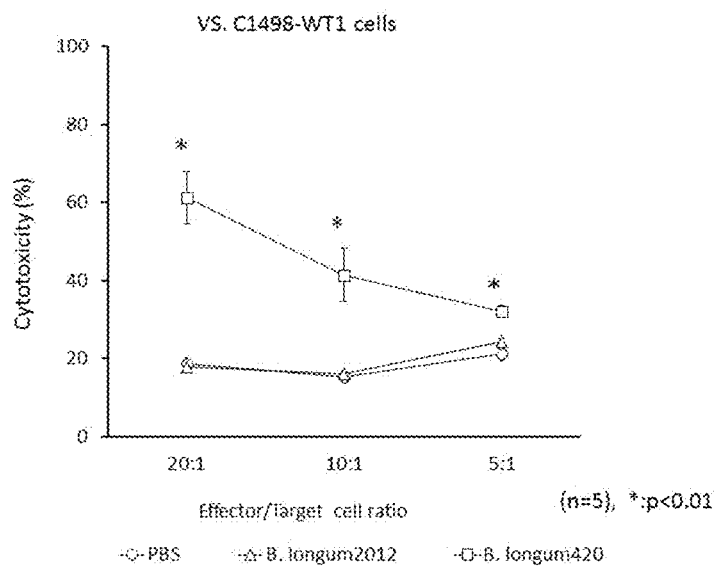
FIGS. 14A and 14B are graphs for showing results of confirmation of the WT1-specific cytotoxic activation capacity of the transformed *Bifidobacterium* of the present invention (Example 4).
Figure 14B:
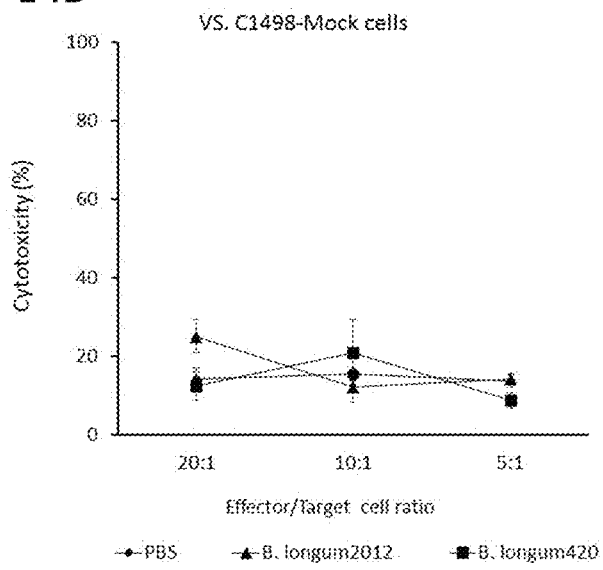

The results are shown in FIGS. 14A and 14B. In all the cell mixing ratios, WT1-specific cytotoxic activity in the B. longum 420-administered group significantly increased ($p<0.01$). Thus, it was found that the oral administration of the GL-BP-WT1 fusion protein of the transformed Bifidobacterium induced CTLs having WT1-specific cytotoxic activity.

Example 5: Confirmation of Anti-Tumor Effect of Oral Administration of GL-BP-WT1 Fusion Protein of Transformed Bifidobacterium 2

An anti-tumor effect achieved when the frozen stock of the transformed Bifidobacterium obtained in Example 1 described above was orally administered to mice was confirmed. An experimental protocol is illustrated in FIG. 15.

1×10$^6$ cells of the C1498-WT1 cells or the C1498-Mock cells were subcutaneously inoculated into C57BL/6N mice (female, 6-week-old) (n=25). After 2 days, the mice were assigned into three groups (n=5), and oral administration of the transformed Bifidobacterium was initiated. At each time of oral administration, the B. longum 420-administered group was administered with 1×10$^9$ CFU in 100 μL of PBS, the B. longum 2012-administered group was administered with 1×10$^9$ CFU in 100 μL of PBS, and the PBS-administered group was administered with 100 μL of PBS. In addition, an anti-tumor effect was evaluated on the basis of the calculated value of the following tumor volume.

Tumor volume (mm$^3$)=Major axis×Minor axis$^2$×1/2  (Equation)

Figure 16A:
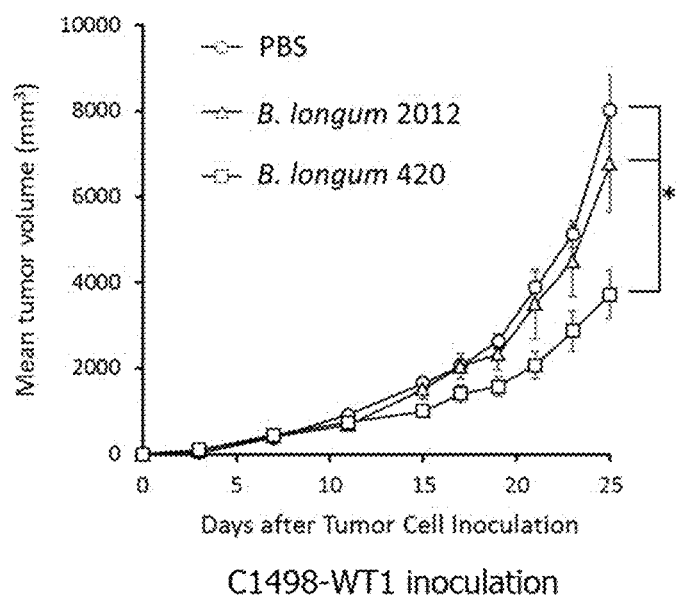
FIGS. 16A and 16B are graphs for showing results of confirmation of the anti-tumor effect of the transformed *Bifidobacterium* of the present invention (Example 5).
Figure 16B:
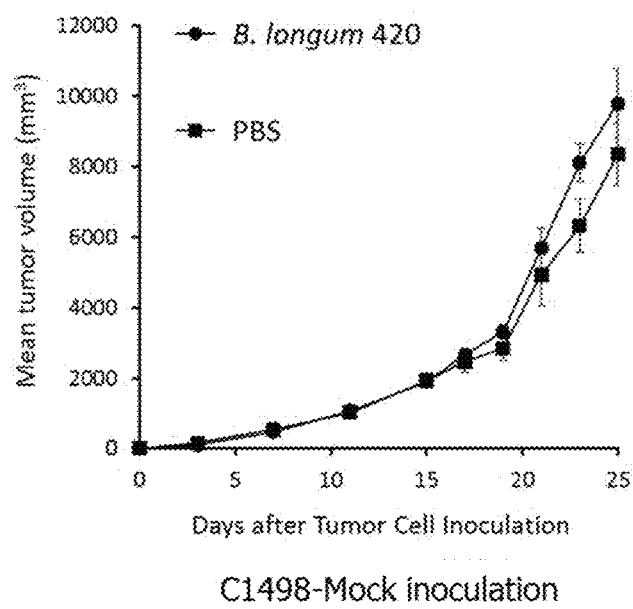

The results are shown in FIG. 16. On Day 25, the tumor volume of the B. longum 420-administered group was significantly inhibited as compared to those in the PBS-administered group and the B. longum 2012-administered group. In addition, an anti-tumor effect on the C1498-Mock cells was not found in the B. longum 420-administered group, and hence it was shown that the anti-tumor effect of the oral administration of the GL-BP-WT1 fusion protein of the transformed Bifidobacterium was specific to WT1-expressing cells.

Example 6: Confirmation of Influence of Adjuvant on Anti-Tumor Effect of Oral Administration of GL-BP-WT1 Fusion Protein of Transformed Bifidobacterium An anti-tumor effect achieved when the frozen stock of the transformed Bifidobacterium obtained in Example 1 described above was orally administered to mice with the use of cholera toxin as an adjuvant for mucosal immunity was confirmed. An experimental protocol is illustrated in FIG. 17.

1×10$^6$ cells of the C1498-WT1 cells were subcutaneously inoculated into the right dorsal area of 6-week-old female C57BL/6N mice. After 7 days, tumor formation was confirmed, the mice were assigned into three groups (n=3), and oral administration of the transformed Bifidobacterium was initiated. At each time of oral administration, the B. longum 420-administered group was administered with 6.4×10$^9$ CFU in 200 μL of PBS, the B. longum 420+cholera toxin-administered group was administered with 6.4×10$^9$ CFU+10 μg of cholera toxin (Wako) in 200 μL of PBS, and the PBS-administered group was administered with 200 μL of PBS. Vaccine administration was performed three times in total on Days 7, 14, and 21 with the day of the tumor inoculation being defined as Day 0. During the period from Day 0 to Day 27, a tumor diameter was measured. An anti-tumor effect was evaluated on the basis of the calculated value of a tumor volume in the same manner as in Example 5.

Figure 18A:
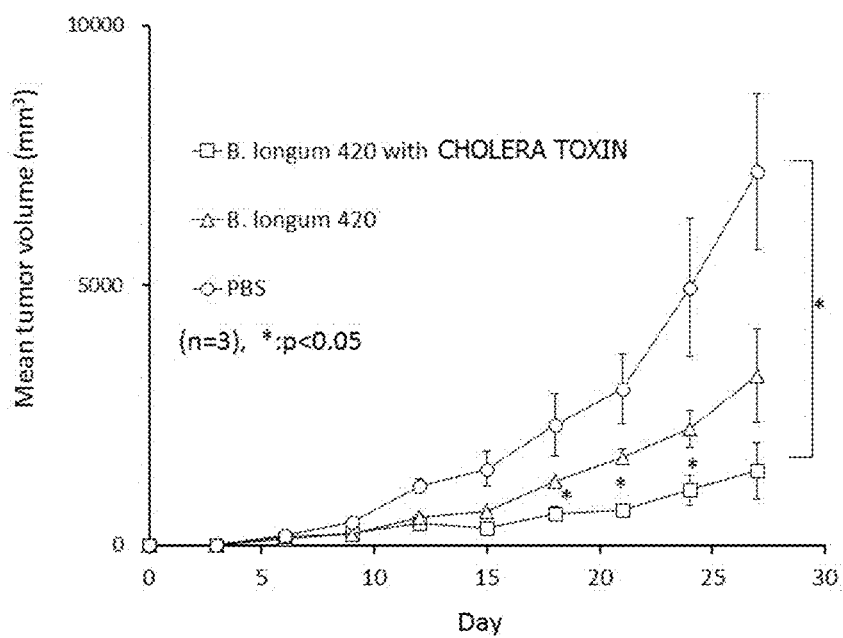
FIGS. 18A and 18B are graphs for showing results of confirmation of the anti-tumor effect of the transformed *Bifidobacterium* of the present invention in combined use with an adjuvant (Example 6).
Figure 18B:
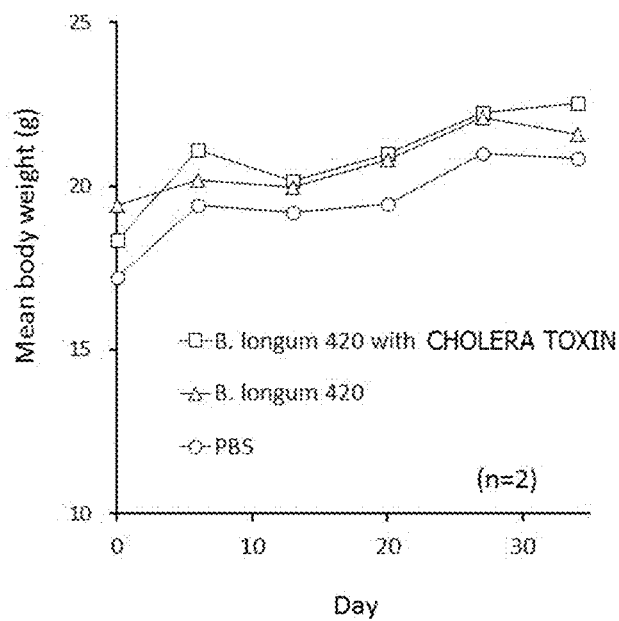

The results are shown in FIGS. 18A and 18B. Through the combined use of B. longum 420 and cholera toxin in weekly administration, a significant anti-tumor effect was found on Day 18 and thereafter as compared to that in the PBS group ($p<0.05$). Mice that had not been inoculated with a tumor were subjected to similar oral administration, and as a result, the mean body weight in the cholera toxin combined use group changed similarly to those in the other groups (the right-hand side of FIGS. 18A and 18B). Side effects, such as diarrhea and a behavioral defect, of the administration were not observed. It was found that the combined use with cholera toxin was able to safely boost the anti-tumor effect in infrequent administration.

(Example 7: Confirmation of Influences of Various Adjuvants for Mucosal Immunity on Anti-Tumor Effect of Oral Administration of GL-BP-WT1 Fusion Protein of Transformed Bifidobacterium)

anti-tumor effect s achieved when the frozen stock of the transformed Bifidobacterium obtained in Example 1 described above was orally administered to mice with the use of various adjuvants for mucosal immunity were confirmed. An experimental protocol is illustrated in FIG. 19.

6-Week-old female C57BL/6N mice were assigned into the following five groups (n=3), and oral administration of the transformed Bifidobacterium was initiated: B. longum 420+20 μg/dose LTB (Heat-Labile Enterotoxin B subunit (Sigma)); B. longum 420+20 μg/dose MPLA (Monophosphoryl Lipid A (Sigma)); B. longum 420+100 μg/dose Chitosan (Chitosan low molecular weight (Sigma); B. longum 420+10 μg/dose CpG 1585 (Invivogen); and PBS.

Each Bifidobacterium administration liquid at 6.4× 10$^9$CFU/200 μL, or 200 μL of PBS was orally administered to the mice using a sonde. On Day 49, the C1498-WT1 cells were subcutaneously inoculated into the right dorsal area, and during the period until Day 76, a tumor diameter was measured. An anti-tumor effect was evaluated on the basis of the calculated value of a tumor volume in the same manner as in Example 6.

Figure 20A:
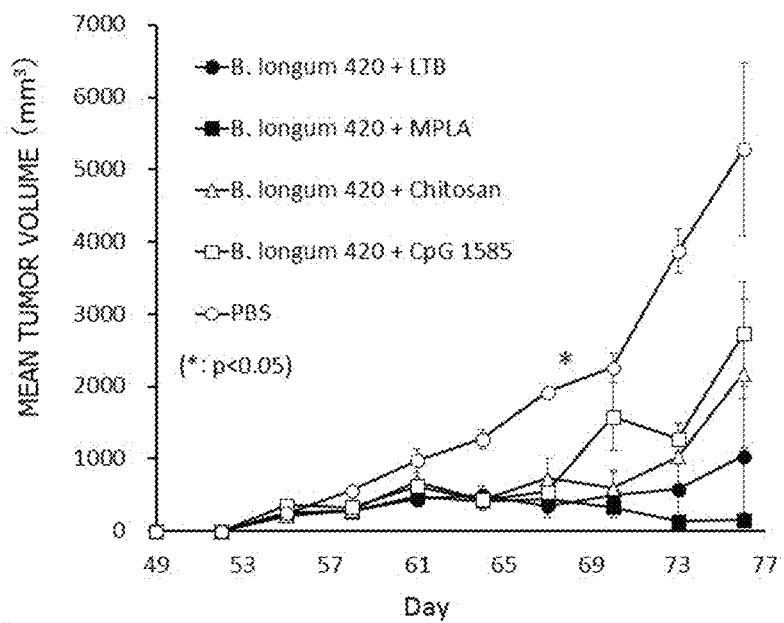
FIGS. 20A and 20B are graphs for showing results of confirmation of the anti-tumor effect of the transformed *Bifidobacterium* of the present invention in combined use with an adjuvant (Example 7).
Figure 20B:
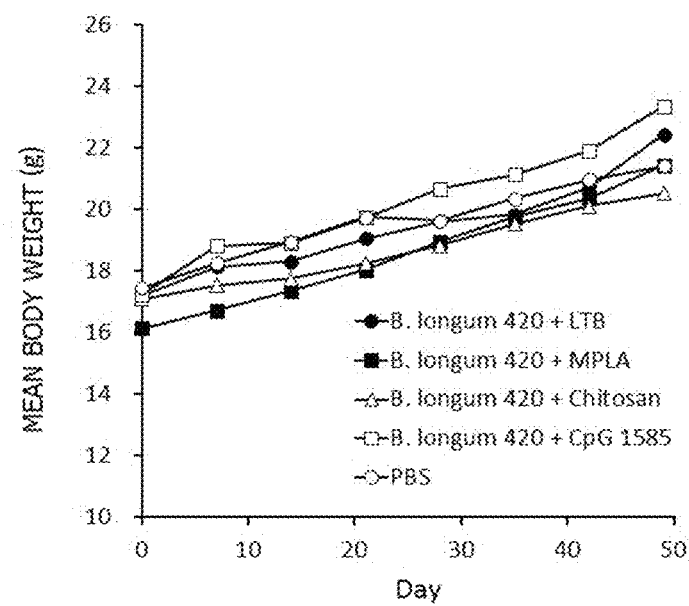

The results are shown in FIGS. 20A and 20B. On Day 67, tumor growth in each of all the adjuvant combined use groups was significantly inhibited as compared to that in the PBS-administered group ($p<0.05$). Significant tumor inhibition was found in each of the LTB and Chitosan combined use groups on Day 70 and in each of the LTB, Chitosan, and CpG1585 combined use groups on Day 73, as compared to that in the PBS group (p<0.05). It was found that the oral administration of the GL-BP-WT1 fusion protein of the transformed *Bifidobacterium* exhibited a preventive anti-tumor effect. During the oral administration period from Day 0 to Day 49, the mean body weight in each of all the adjuvant combined use groups changed similarly to that in the PBS group. Side effects, such as diarrhea and a behavioral defect, of the administration were not found.

Example 8: Generation of *Bifidobacterium* Displaying GL-BP-WT1 on Surface Thereof 2

A. the isolation of a GL-BP gene and B. the construction of a pMW118 plasmid having an isolated GL-BP gene were performed by the same techniques as those of Example 1.

C. Isolation of WT1 Gene

DNA encoding an amino acid sequence from position 117 to position 439 of human WT1 (SEQ ID NO: 15) was obtained by total synthesis (Funakoshi Co., Ltd.). In the synthesis, codons frequently used in a *Bifidobacterium* were used. In addition, an XhoI recognition sequence (CTCGAG: SEQ ID NO: 5) was added to the N-terminus side, and a stop codon and a succeeding SphI recognition sequence (GCATGC: SEQ ID NO: 6) were added to the C-terminus side. The DNA was introduced into the SmaI site of a pUC18 vector to construct a plasmid. DNA Ligation Kit Ver. 2 (manufactured by Takara Bio Inc.) was used for ligation. The constructed plasmid was transferred into *E. coli* DH5α (manufactured by Takara Bio Inc.) by a heat shock method (42° C., 30 seconds). The resultant was applied to an LB agar medium containing 100 μg/ml of ampicillin (manufactured by Difco), and was cultured at 37° C. overnight to provide transformed *E. coli* harboring a plasmid having DNA encoding a human WT1 protein (117 to 439). The plasmid was extracted and purified from the transformed *E. coli* using Quantum Prep Plasmid Miniprep Kit (manufactured by Bio-Rad), and its sequence was confirmed by sequencing.

```
Sequence of synthesized human WT1 gene
                                      (SEQ ID NO: 15)
CCGTCCCAGGCGTCGTCGGGCCAGGCGAGGATGTTCCCGAACGCGCCCTA

CCTGCCCAGCTGCCTGGAGTCCCAGCCGGCGATCCGCAACCAGGGCTACT

CCACCGTGACGTTCGACGGCACCCCGTCCTACGGCCACACGCCCAGCCAC

CACGCCGCCCAGTTCCCGAACCACAGTTCAAGCACGAAGACCCCATGGG

CCAGCAGGGCAGCCTCGGCGAACAGCAGTACAGCGTGCCGCCGCCGGTCT

ACGGCTGCCACACCCCGACCGACTCCTGCACGGGCTCCCAGGCCCTGCTC

CTGCGTACGCCGTACTCCTCCGACAACCTCTACCAGATGACCTCCCAGCT

GGAGTGCATGACCTGGAACCAGATGAACCTGGGCGCCACGCTGAAGGGAG

TCGCCGCGGGGTCGTCGAGCTCCGTCAAGTGGACCGAAGGCCAGTCCAAC

CACTCCACCGGCTACGAGTCCGACAACCACACCACGCCGATCCTGTGCGG

AGCCCAGTACCGCATCCACACGCACGGCGTCTTCCGCGGCATCCAGGACG

TCCGGCGCGTCCCCGGCGTCGCGCCGACCCTGGTGCGGTCCGCCTCCGAG

ACCTCCGAGAAGCGCCCGTTCATGTGCGCCTACCCGGGCTGCAACAAGCG

CTACTTCAAGCTCTCGCACCTGCAGATGCACTCCCGGAAGCACACCGGCG
```

```
AGAAGCCGTACCAGTGCGACTTCAAGGACTGCGAACGCCGCTTCTCGCGC

AGCGACCAGCTGAAGCGCCACCAGCGTAGGCACACCGGCGTGAAGCCCTT

CCAGTGCAAGACCTGCCAGCGCAAGTTCTCCCGCAGCGACCACCTCAAGA

CGCACACCCGCACCCACACCGGCAAGACGTCCGAGAAGCCGTTCTCGTGC

CGCTGGCCCAGCTGCCAGAAGAAGTTCGCCCGCAGCGACGAGCTCGTGCG

CCACCACAACATGCACCAGTGAA
```

In addition, DNA encoding a mutant WT1 protein having an amino acid sequence having a M236Y substitution introduced into an HLA-A*2402-restrictive CTL epitope in an amino acid sequence from position 117 to position 439 of human WT1 was obtained by total synthesis in the same manner as above, and a recombinant plasmid was generated.

```
Sequence of synthesized human WT1 gene
                                      (SEQ ID NO: 17)
CCGTCCCAGGCGTCGTCGGGCCAGGCGAGGATGTTCCCGAACGCGCCCTA

CCTGCCCAGCTGCCTGGAGTCCCAGCCGGCGATCCGCAACCAGGGCTACT

CCACCGTGACGTTCGACGGCACCCCGTCCTACGGCCACACGCCCAGCCAC

CACGCCGCCCAGTTCCCGAACCACAGCTTCAAGCACGAAGACCCCATGGG

CCAGCAGGGCAGCCTCGGCGAACAGCAGTACAGCGTGCCGCCGCCGGTCT

ACGGCTGCCACACCCCGACCGACTCCTGCACGGGCTCCCAGGCCCTGCTC

CTGCGTACGCCGTACTCCTCCGACAACCTCTACCAGATGACCTCCCAGCT

GGAGTGCTACACCTGGAACCAGATGAACCTGGGCGCCACGCTGAAGGGAG

TCGCCGCGGGGTCGTCGAGCTCCGTCAAGTGGACCGAAGGCCAGTCCAAC

CACTCCACCGGCTACGAGTCCGACAACCACACCACGCCGATCCTGTGCGG

AGCCCAGTACCGCATCCACACGCACGGCGTCTTCCGCGGCATCCAGGACG

TCCGGCGCGTCCCCGGCGTCGCGCCGACCCTGGTGCGGTCCGCCTCCGAG

ACCTCCGAGAAGCGCCCGTTCATGTGCGCCTACCCGGGCTGCAACAAGCG

CTACTTCAAGCTCTCGCACCTGCAGATGCACTCCCGGAAGCACACCGGCG

AGAAGCCGTACCAGTGCGACTTCAAGGACTGCGAACGCCGCTTCTCGCGC

AGCGACCAGCTGAAGCGCCACCAGCGTAGGCACACCGGCGTGAAGCCCTT

CCAGTGCAAGACCTGCCAGCGCAAGTTCTCCCGCAGCGACCACCTCAAGA

CGCACACCCGCACCCACACCGGCAAGACGTCCGAGAAGCCGTTCTCGTGC

CGCTGGCCCAGCTGCCAGAAGAAGTTCGCCCGCAGCGACGAGCTCGTGCG

CCACCACAACATGCACCAGTGAA
```

D. the construction of a plasmid having a WT1 gene downstream of a GL-BP gene, E. the construction of an *E. coli*-*Bifidobacterium* shuttle vector, F. the integration of a gene having a GL-BP gene and a WT1 gene linked to each other into an *E. coli*-*Bifidobacterium* shuttle vector pJW241, and G. the preparation of a host *Bifidobacterium* liquid were performed in the same manner as in Example 1 to generate two kinds of transformed *Bifidobacterium*.

Figure 21:
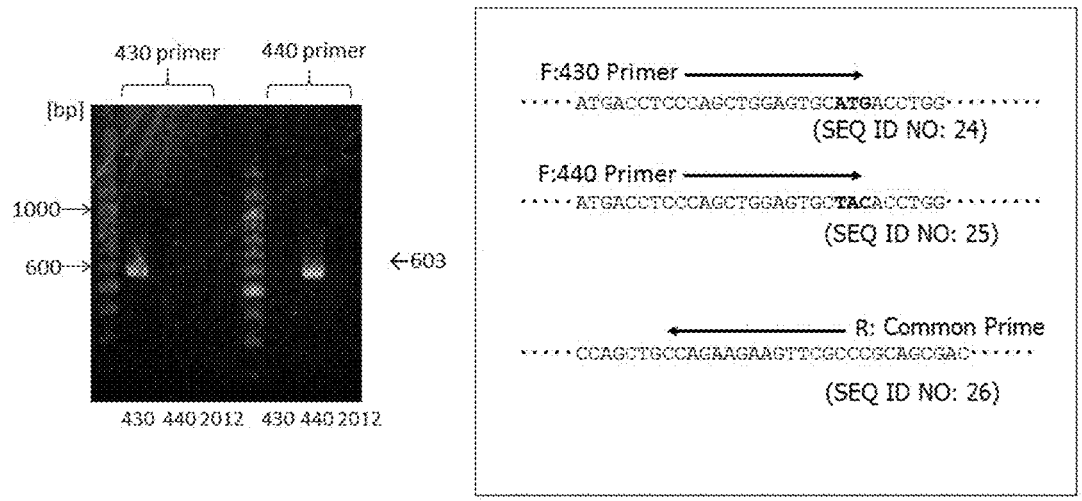
FIG. 21 is an image for showing results of confirmation of DNA encoding a WT1 protein at the gene level in the transformed *Bifidobacterium* of the present invention (Example 8).

FIG. 21 is an image for showing that the two kinds of transformed *Bifidobacterium* were identified at the gene level using specific primers shown on the right-hand side of FIG. 21. 430 represents *B. longum* 430, which is a *Bifidobacterium* transformed with a shuttle vector having inserted therein DNA encoding a human WT1 protein (117 to 439). 440 represents *B. longum* 440, which is a *Bifidobacterium* transformed with a shuttle vector having inserted therein DNA encoding a human WT1 protein (117 to 439) having an amino acid substitution M236Y. As in Example 1, 2012 represents *B. longum* 2012, which is a *Bifidobacterium* transformed with a shuttle vector having inserted therein only a GLBP gene without having inserted therein DNA encoding WT1. The primer denoted by 430 amplifies the DNA encoding the human WT1 protein (117 to 439), and the primer denoted by 440 amplifies the DNA encoding the human WT1 protein (117 to 439) having an amino acid substitution M236Y.

Example 9: Confirmation of Displaying of GL-BP-WT1 Fusion Protein of Transformed *Bifidobacterium* on Surface Thereof For each transformed *Bifidobacterium* obtained in Example 8 described above, the expression of the GL-BP-WT1 fusion protein on its surface was confirmed by the same technique as that of Example 2.

Figure 22A:
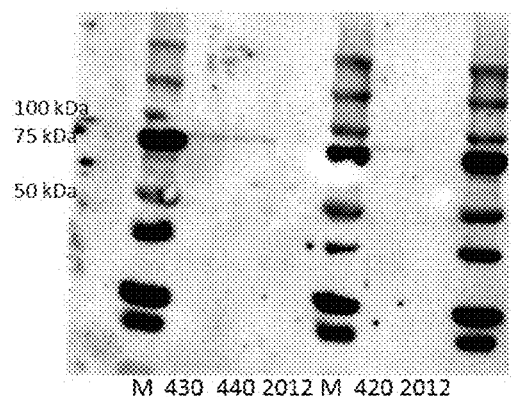
FIGS. 22A and 22B are photographic images for showing: results of confirmation by western blotting of a WT1 protein expressed on the surface of the transformed *Bifidobacterium* of the present invention (FIG. 22A); and results of confirmation thereof by immunofluorescence staining (FIG. 22B) (Example 9).
Figure 22B:
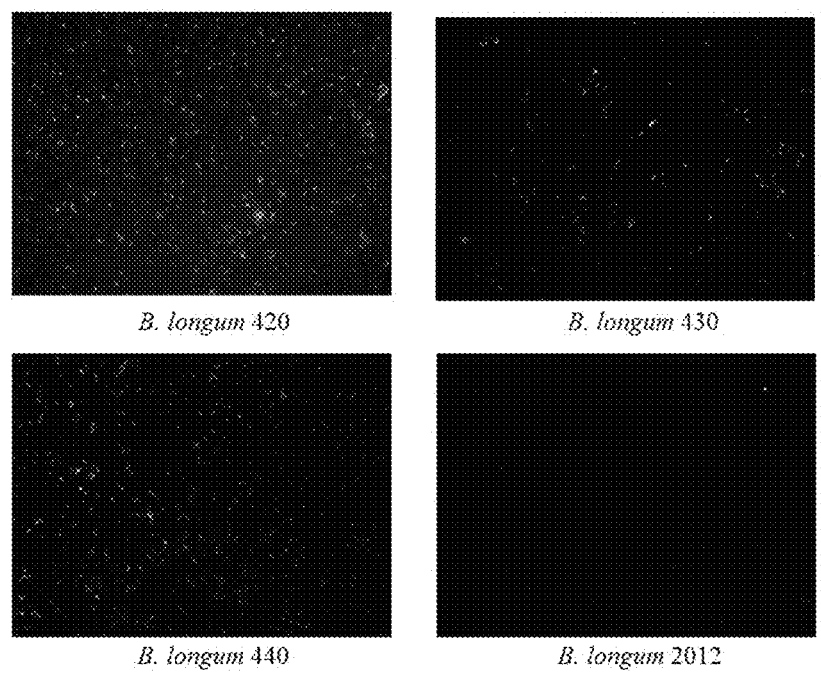

The results of western blotting are shown in FIG. 22A, and the results of immunofluorescence staining are shown in FIG. 22B. As apparent from FIGS. 22A and 22B, *B. longum* 430 and *B. longum* 440 each showed a band at about 82.5 kDa corresponding to the sum of the molecular weights of WT1 and the GL-BP fusion protein as with *B. longum* 420.

In addition, it was confirmed from the fluorescence micrographs that WT1 was present on the cell surface of each of *B. longum* 430 and *B. longum* 440. Therefore, it was confirmed that each transformed *Bifidobacterium* expressed a GL-BP-WT1 fusion protein.

INDUSTRIAL APPLICABILITY

As described in detail above, according to the transformed *Bifidobacterium* of the present invention, the WT1 protein can be expressed and displayed on the cell surface of the *Bifidobacterium*. By virtue of displaying a WT1 antigen protein on the surface of the *Bifidobacterium*, the transformed *Bifidobacterium* can be utilized as an oral vaccine effective for a tumor expressing a WT1 protein. The oral vaccine is easy to ingest even for a child or an elderly person, and besides, is free of pain involved in vaccine inoculation by general injection. In particular, the oral vaccine of the present invention is highly safe by virtue of the use of the *Bifidobacterium*, which has an experience in food. In addition, the antigen WT1 protein of the present invention is the *Bifidobacterium* capable of expressing a WT1 protein covering most of the sequence of WT1 unlike a WT1 peptide restricted to a certain HLA. The cancer vaccine using the transformed *Bifidobacterium* as an active ingredient is applicable to patients of various HLA types.

The invention claimed is:

1. An oral formulation, comprising a transformed *Bifidobacterium* as an active ingredient of a vaccine, wherein
the transformed *Bifidobacterium* comprises:
DNA encoding a WT1 protein; and
DNA encoding a GNB/LNB substrate-binding membrane protein derived from a *Bifidobacterium*,
the transformed *Bifidobacterium* being designed to display the WT1 protein as an antigen on a surface of the transformed *Bifidobacterium*.

2. The oral formulation according to claim 1, wherein the formulation comprises a cancer vaccine formulation.

3. The oral formulation according to claim 2, further comprising an adjuvant.

4. An oral formulation, comprising a transformed *Bifidobacterium* as an active ingredient of a vaccine, wherein
the transformed *Bifidobacterium* comprises:
DNA encoding a WT1 protein; and
DNA encoding a GNB/LNB substrate-binding membrane protein derived from a *Bifidobacterium*,
the transformed *Bifidobacterium* being designed to display the WT1 protein as an antigen on a surface of the transformed *Bifidobacterium*, and wherein
the WT1 protein comprises any one of the following items 1) to 3):

1) a protein identified by an amino acid sequence identified by SEQ ID NO: 1;
2) a protein identified based on an amino acid sequence having one to sixty amino acids substituted, deleted, added, or introduced in the amino acid sequence identified by SEQ ID NO: 1, the protein having immunogenicity as a vaccine; and
3) a protein identified based on an amino acid sequence having 80% or more homology to the amino acid sequence identified by SEQ ID NO: 1, the protein having immunogenicity as a vaccine.

5. The oral formulation according to claim 1, wherein the WT1 protein comprises at least two of a T cell epitope of SEQ ID NO: 18, a T cell epitope of SEQ ID NO: 19, a T cell epitope of SEQ ID NO: 20, and a T cell epitope of SEQ ID NO: 21.

6. The oral formulation according to claim 1, wherein the transformed *Bifidobacterium* displays the WT1 protein as an antigen on a surface of the transformed *Bifidobacterium*.

7. The oral formulation according to claim 1, wherein the WT1 protein is displayed on a cell surface as a fusion protein of the WT1 protein and the GNB/LNB substrate-binding membrane protein (GL-BP-WT1 fusion protein).

* * * * *